(12) United States Patent
Virr

(10) Patent No.: US 9,968,754 B2
(45) Date of Patent: May 15, 2018

(54) REMOVABLE AND/OR REPLACEABLE HUMIDIFIER

(71) Applicant: ResMed Limited, Bella Vista (AU)

(72) Inventor: Alexander Virr, Mangrove Mountain (AU)

(73) Assignee: RESMED LIMITED, Bella Vista (AU)

( * ) Notice: Subject to any disclaimer, the term of this patent is extended or adjusted under 35 U.S.C. 154(b) by 564 days.

(21) Appl. No.: 14/016,797

(22) Filed: Sep. 3, 2013

(65) Prior Publication Data

US 2014/0001658 A1 Jan. 2, 2014

Related U.S. Application Data

(63) Continuation of application No. 12/213,958, filed on Jun. 26, 2008, now Pat. No. 8,550,075.

(30) Foreign Application Priority Data

Jun. 28, 2007 (AU) .................................. 2007903508

(51) Int. Cl.
*A61M 16/10* (2006.01)
*A61M 16/16* (2006.01)
(Continued)

(52) U.S. Cl.
CPC ...... *A61M 16/1045* (2013.01); *A61M 16/022* (2017.08); *A61M 16/109* (2014.02); *A61M 16/1075* (2013.01); *A61M 16/142* (2014.02); *A61M 16/16* (2013.01); *A61M 16/202* (2014.02); *H05B 6/108* (2013.01); *A61M 16/161* (2014.02); *A61M 2205/3368* (2013.01); *A61M 2205/3606* (2013.01);
(Continued)

(58) Field of Classification Search
CPC .............. A61M 16/10; A61M 16/1075; A61M 16/108; A61M 16/109; A61M 16/14; A61M 16/142; A61M 16/16; A61M 16/162; F24F 6/00; F24F 6/02; B01F 3/02; B01F 3/022
See application file for complete search history.

(56) References Cited

U.S. PATENT DOCUMENTS 3,854,440 A 2/1975 Giocoechea
3,871,373 A 3/1975 Jackson
(Continued)

FOREIGN PATENT DOCUMENTS

AU 2006906224 11/2006
WO WO 2006/069415 7/2006
(Continued)

OTHER PUBLICATIONS

All About Nafion and FAQ—Perma Pure LLCPerma Pure LLC. Captured Feb. 19, 2015.*
(Continued)

*Primary Examiner* — Kathryn E Ditmer
(74) *Attorney, Agent, or Firm* — Nixon & Vanderhye, P.C.

(57) ABSTRACT

Humidifier apparatus for a respiratory apparatus includes a housing providing a gas flow path, a heater apparatus, and a water supply distribution member configured and arranged to deliver water vapor to the gas flow path. The water distribution member is provided to the housing and in thermal communication with the heater apparatus.

29 Claims, 19 Drawing Sheets

(51) Int. Cl.
*H05B 6/10* (2006.01)
*A61M 16/14* (2006.01)
*A61M 16/20* (2006.01)
*A61M 16/00* (2006.01)

(52) U.S. Cl.
CPC .............. *A61M 2205/368* (2013.01); *A61M 2205/3653* (2013.01); *A61M 2205/3673* (2013.01); *A61M 2205/7509* (2013.01); *A61M 2205/7518* (2013.01); *Y10T 137/474* (2015.04)

(56) References Cited

U.S. PATENT DOCUMENTS

| | | | | |
|---|---|---|---|---|
| 4,012,473 | A * | 3/1977 | Lindsey | A61M 11/06 128/200.13 |
| 4,098,853 | A | 7/1978 | Brown et al. | |
| 4,146,597 | A | 3/1979 | Eckstein et al. | |
| 4,155,961 | A | 5/1979 | Benthin | |
| 4,532,088 | A | 7/1985 | Miller | |
| 4,657,713 | A | 4/1987 | Miller | |
| 4,715,998 | A * | 12/1987 | Clow | A61M 16/16 128/203.17 |
| 4,753,758 | A * | 6/1988 | Miller | A61M 16/162 128/203.17 |
| 4,793,123 | A * | 12/1988 | Pharo | B65D 81/052 206/522 |
| 4,847,470 | A * | 7/1989 | Bakke | A61M 5/44 165/170 |
| 4,898,585 | A * | 2/1990 | Borsanyi | A61M 5/1428 604/153 |
| 4,910,384 | A | 3/1990 | Silver | |
| 4,921,642 | A | 5/1990 | LaTorraca | |
| 4,943,704 | A | 7/1990 | Rabenau | |
| 5,943,704 | A | 7/1990 | Levine | |
| 4,955,372 | A * | 9/1990 | Blackmer | A61D 7/04 128/203.16 |
| 5,062,145 | A * | 10/1991 | Zwaan | A61M 16/16 392/395 |
| 5,245,693 | A * | 9/1993 | Ford | A61M 5/44 165/169 |
| 5,348,691 | A | 9/1994 | McElroy et al. | |
| 5,564,415 | A | 10/1996 | Dobson et al. | |
| 5,595,690 | A * | 1/1997 | Filburn | F24F 6/04 261/104 |
| 6,201,223 | B1 * | 3/2001 | Nitta | A61M 16/1075 219/544 |
| 6,766,817 | B2 | 7/2004 | da Silva | |
| 6,918,404 | B2 | 7/2005 | da Silva | |
| 7,066,586 | B2 | 6/2006 | da Silva | |
| 7,146,979 | B2 | 12/2006 | Seakins et al. | |
| 7,164,852 | B2 * | 1/2007 | Cazzini | A61M 5/445 392/470 |
| 7,244,398 | B2 | 7/2007 | Kotary et al. | |
| 7,285,255 | B2 | 10/2007 | Kadlec et al. | |
| 7,320,261 | B1 * | 1/2008 | Hockaday | A61F 9/028 73/865.6 |
| 2004/0074493 | A1 | 4/2004 | Seakins et al. | |
| 2006/0014059 | A1 * | 1/2006 | Wood | C01B 3/065 429/413 |
| 2006/0021615 | A1 | 2/2006 | Kertzman | |
| 2006/0037613 | A1 | 2/2006 | Kwok et al. | |
| 2006/0118111 | A1 | 6/2006 | Pelerossi et al. | |
| 2006/0191531 | A1 | 8/2006 | Mayer et al. | |
| 2006/0201506 | A1 | 9/2006 | Makinson et al. | |
| 2007/0125376 | A1 | 6/2007 | Reinstadtler | |
| 2007/0157927 | A1 | 7/2007 | Levine | |

FOREIGN PATENT DOCUMENTS

| | | | |
|---|---|---|---|
| WO | PCT/AU2007/000274 | 3/2007 | |
| WO | WO 2007/101298 | 9/2007 | |
| WO | WO 2008/055307 | 5/2008 | |
| WO | WO 2010039051 A2 * | 4/2010 | .......... A61M 16/162 |

OTHER PUBLICATIONS

Unsolicited email from Elson Silva, PhD, dated Jan. 2, 2009, "Understanding Hydrology in the Patenting Systemm—U.S. Pat. 2009/0000620," (email provided in both HTML and plain text format).

* cited by examiner

REMOVABLE AND/OR REPLACEABLE HUMIDIFIER

CROSS-REFERENCE TO APPLICATION

This application is a continuation of U.S. patent application Ser. No. 12/213,958, filed Jun. 26, 2008, which claims priority to Australian Application No. AU 2007903508, filed Jun. 28, 2007, the entire contents of each which is incorporated herein by reference in their entirety.

BACKGROUND OF THE INVENTION

1. Field of the Invention

The present invention relates to humidification arrangements used to control the humidity of breathable gases used in respiratory apparatus ventilation systems including invasive and non-invasive ventilation, Continuous Positive Airway Pressure (CPAP), Bi-level therapy and treatment for sleep disordered breathing (SDB) conditions such as Obstructive Sleep Apnea (OSA), and for various other respiratory disorders and diseases.

2. Description of the Art

Respiratory apparatus commonly have devices to alter the humidity of the breathable gas in order to reduce drying of the patient's airway and consequent patient discomfort and associated complications. The use of a humidifier placed between the positive airway pressure device (or flow generator) and the patient mask produces humidified gas that minimizes drying of the nasal mucosa and increases patient airway comfort.

Many humidifier types have been proposed, including humidifiers that are either integrated with or configured to be coupled to the relevant respiratory apparatus. While passive humidifiers can provide some relief, generally a heated humidifier is required to provide sufficient humidity and temperature to the air so that patient will be comfortable.

Humidifiers typically comprise a water tub having a capacity of several hundred milliliters, a heating element for heating the water in the tub, a control to enable the level of humidification to be varied, a gas inlet to receive gas from the positive airway pressure device, and a gas outlet adapted to be connected to a gas conduit that delivers the humidified pressurized gas to the patient's mask.

Tub-of-water humidifiers are vulnerable to liquid water spillage if they are not maintained in a substantially vertical orientation. Spillage of liquid water can either travel into the gas conduit to the patient or back into the positive airway pressure device and associated electronics or deplete the reservoir of humidifying water. In either of the cases, the spillage of water is undesirable.

A semi-permeable membrane may be used to isolate the liquid water from the gas flow. The semi-permeable membrane has the characteristic of allowing water vapour to pass through it but not liquid water. Water vapour passing through the semi-permeable membrane may be entrained into the gas flow within the humidifier and then passed to the patient.

U.S. Pat. Nos. 3,871,373, 4,146,597 and 4,155,961 disclose the use of tubes of semi-permeable membrane, containing liquid water, inserted into the gas flow path. The tubes are used as a source of water vapour for entraining into the passing gas flow stream.

U.S. Pat. Nos. 4,753,758 and 4,921,642 disclose the use of a semi-permeable membrane to separate a water chamber and a gas flow path chamber of a humidifier. In these examples, the water and gas flow chambers are typically generous in their volumes with consequently a high thermal capacity and slow thermal response.

U.S. Pat. Nos. 4,910,384 and 5,062,145 disclose a heater situated within a water-containing envelope of semi-permeable membrane material, dividing the gas chamber in two.

In U.S. Pat. No. 4,657,713, a heater block of the humidifier incorporates a water supply and a semi-permeable filter membrane.

None of these prior art devices provide a satisfactory solution to the provision of humidified breathable gas to the patient, nor to the ease of construction, disposability, retrofitting and hygiene requirements for a humidification device.

SUMMARY OF THE INVENTION

One aspect of the present invention relates to a humidifier apparatus which overcomes or ameliorates disadvantages of the prior art.

In one embodiment, a humidifier apparatus comprises a housing which includes a gas inlet and outlet for the gas flow, a water supply distribution member that supplies water vapour to the gas flow and a heater apparatus that is in thermal contact with the water supply distribution member. The water supply distribution member has adaptations so that it is a removable and replaceable fitting to the humidifier apparatus.

In an embodiment, at least a part of the heater apparatus is also a removable and replaceable fitting to the humidifier apparatus.

In a further embodiment, aspects of the humidifier apparatus may be disposable or the humidifier apparatus may provide one or more sub-components which may be removable for either replacement or re-use after servicing. For example, a thin, envelope form of the water supply distribution member may be disposable.

A further aspect of the invention provides that part of the heater apparatus forms part of the water distribution member. In an embodiment, this part of the heater apparatus may be an induction receiving element.

In an embodiment, the water supply distribution member may include a wick and/or capillary action device which provides water for vaporization into the gas flow.

A further aspect of the invention relates to a humidity control device which enables the amount of water vapour passing from the water distribution member to the gas flow to be controlled.

In an embodiment, the water supply distribution member may include a water filter.

In an embodiment, the gas flow path, the water distribution member and at least a part of the heater apparatus are located in the humidifier apparatus as a number of thin, adjacent layers. The thin layering of each of these components serves to improve the vaporization of the water and its mixing into the gas flow.

Another aspect of the invention relates to a humidifier apparatus for a respiratory apparatus including a housing providing a gas flow path, a heater apparatus, and a water supply distribution member configured and arranged to deliver water vapour to the gas flow path. The water distribution member is provided to the housing and in thermal communication with the heater apparatus.

Another aspect of the invention relates to a humidifier apparatus for a respiratory apparatus including a housing, one or more water supply distribution members removably fitted to the housing, and a heater apparatus in thermal communication with at least one of the water distribution members. The one or more water supply distribution members are configured and arranged to deliver water vapour to one or more gas flow paths defined by the one or more water supply distribution members and the housing.

Another aspect of the invention relates to a water distribution member for a humidifier apparatus including an envelope formed by a first compartment wall and a second compartment wall joined together, and a water inlet into the envelope.

Another aspect of the invention relates to a humidifier apparatus including a base plate removably and replaceably attachable to a humidifier housing, a heater apparatus provided to the base plate, and a water distribution member provided to the base plate. The water distribution member includes first and second compartment walls that define an envelope adapted to receive a supply of water. The first compartment wall includes a semi-permeable membrane adapted to allow water vapour to pass therethrough and the second compartment wall includes a thermally conductive wall in thermal communication with the heater apparatus.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

FIGS. 1 to 5 schematically show a first embodiment of a humidifier apparatus 110 for delivering water vapour into a breathable gas flow produced by a positive airway pressure device (or flow generator) of a respiratory apparatus such as a Continuous Positive Airway Pressure (CPAP) therapy machine.

Figure 1:
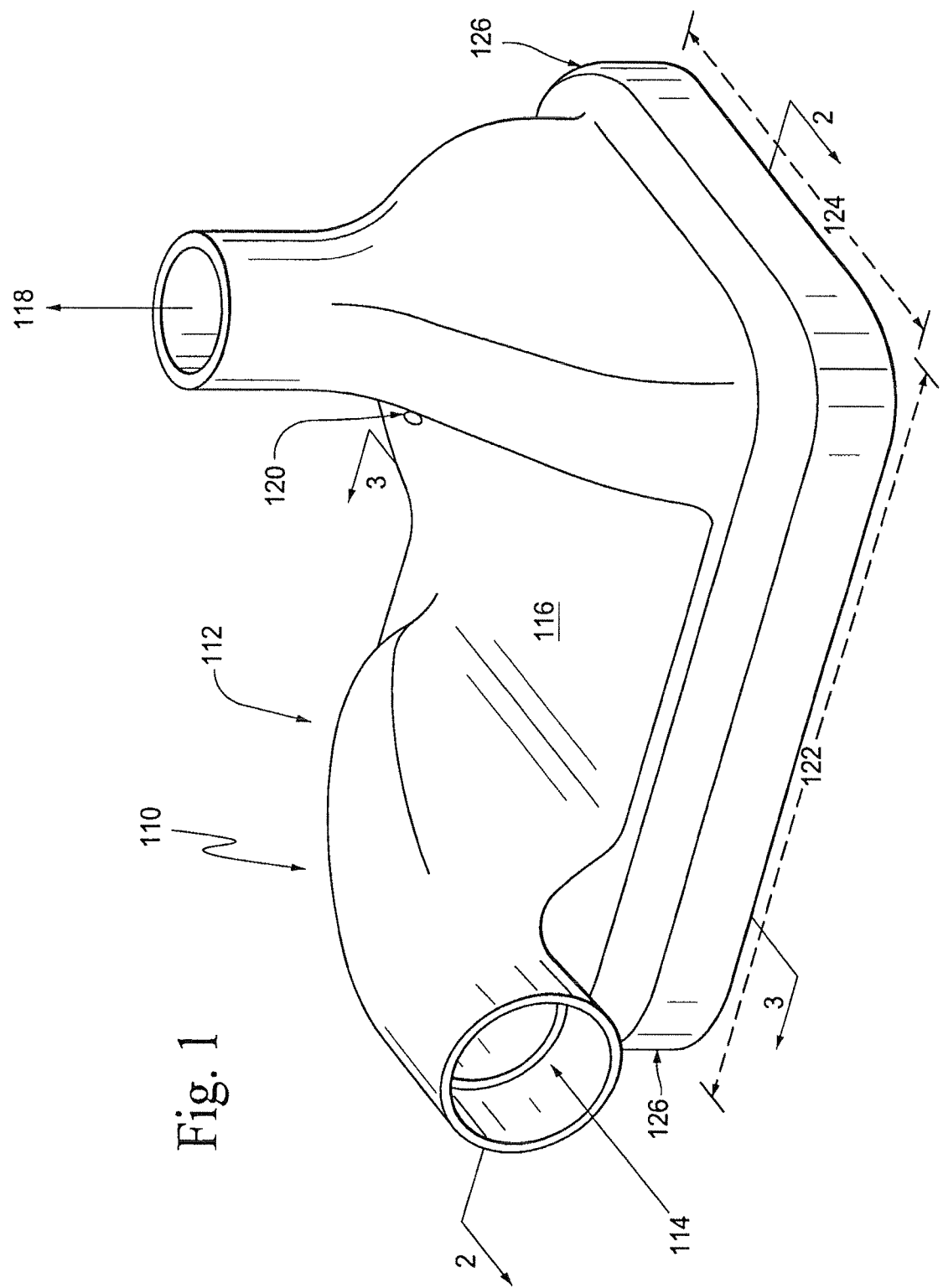
FIG. 1 is a schematic perspective view of a humidifier apparatus according to an embodiment of the present invention.

With reference to FIG. 1, the humidifier has a housing 112 which defines an upper internal gas flow path, described below with reference to FIG. 2. The housing 112 includes a gas inlet 114, which receives gas flow (indicated by an arrow) from the positive airway pressure device (not shown), a low-profile centre section 116 and gas outlet 118.

In use, the gas outlet 118 of humidified breathable gas flow (indicated by an arrow) is typically connected to a patient conduit (not shown) which in turn is connected to the patient's mask. The form of the connectors for the gas inlet 114 and the gas outlet 118 may be of any suitable, conventional connector to enable connection to the positive airway pressure device and the patient conduit. The housing 112 also may have a water inlet passage 120 adapted for connection to a supply of liquid water for the humidifier apparatus. The water supplied is used for the humidification of the gas passing through the humidifier apparatus 110.

The housing 112 of the humidifier apparatus 110, as shown in FIG. 1, may be of a material that is light, durable to heat and water and approved as safe for use in respiratory medical apparatus. In addition, the material may be sufficiently resilient to allow easy connection of the appropriate fittings to the gas inlet 114 and the gas outlet 118. Preferable materials for the housing are resilient plastic like materials, for example polycarbonate, polycarbonate ABS blends or polypropylene. However, the housing may be constructed of other suitable materials.

In one embodiment, the housing 112 as shown in FIG. 1 may be generally rectangular in plan view with example dimensions of: approximate length 122 of 120 to 150 mm and a breadth 124 of 100 to 120 mm. The housing 112 may also have a downwardly extending peripheral flange 126 approximately 5 to 20 mm in height. The dimensions and shape of the housing 112 given here and later are given by way as examples for the embodiments described here. Other dimensions and shapes to those given may also be used, for example depending on the humidification capacity of the humidifier apparatus 110 and/or for compatibility with respiratory apparatus.

Figure 2:
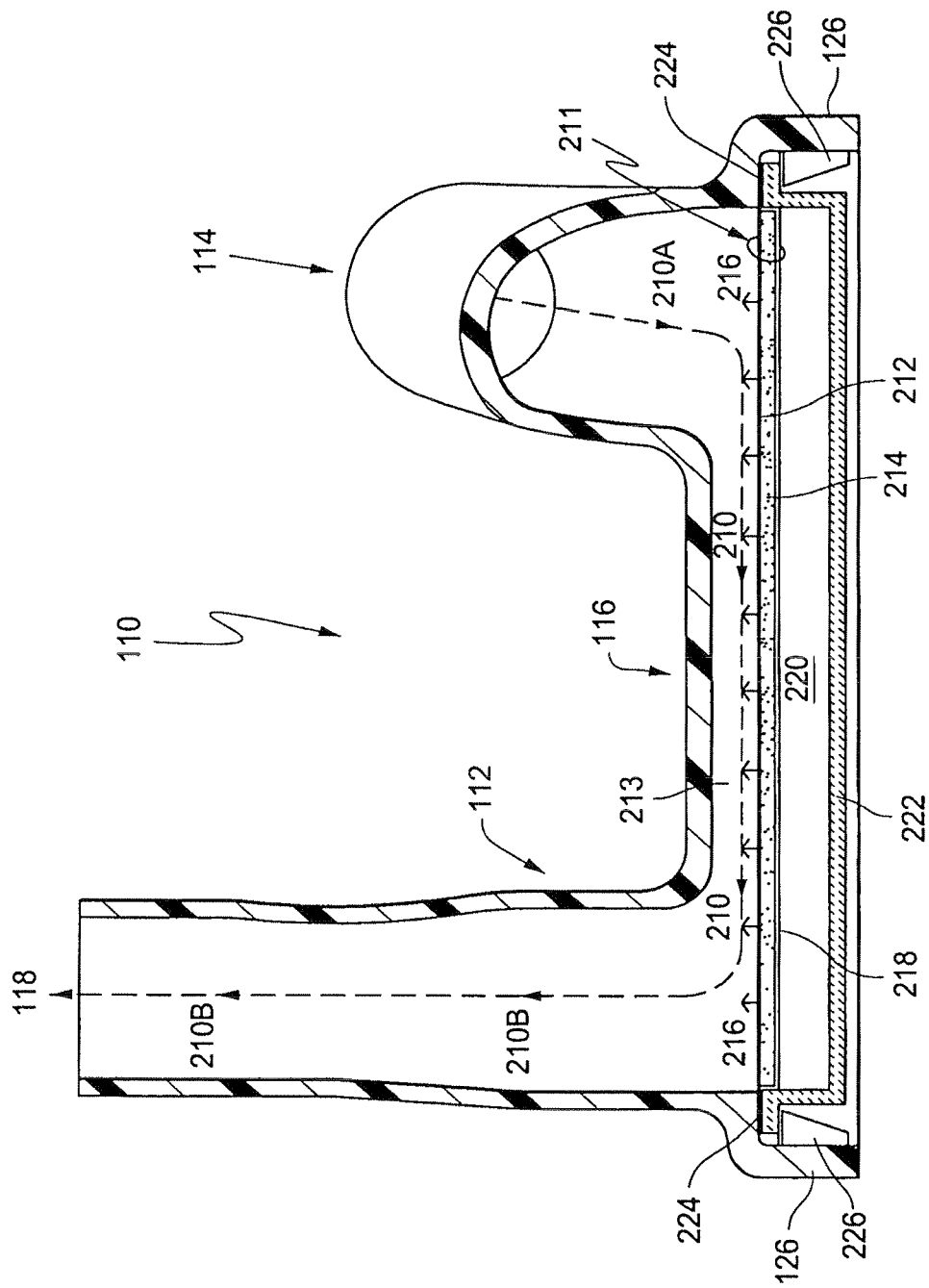
FIG. 2 is a cross-sectional view taken along the line 2-2 of FIG. 1.

FIG. 2 is a cut away view taken along line 2-2 in FIG. 1, showing the internal components and gas flow path 210 (indicated by the arrows), within the humidifier apparatus 110.

The gas flow path 210 flows through the low profile centre section 116 of the housing 112 and over a water distribution member 211 that has a first compartment wall 212 which separates a liquid water layer 214 from the gas flow path 210. The low profile centre section 116 of the housing 112 and the first compartment wall 212 form a gas passage layer 213 between the gas inlet 114 and gas outlet 118. The gas flow 210 receives water vapour 216 through the first compartment wall 212 into the gas passage layer 213, as indicated by arrows, so that ambient gas 210A entering the humidifier apparatus 110 is humidified in the low profile centre section 116 and exits as humidified gas 210B.

A second compartment wall 218, which is also part of the water distribution member 211, separates the water layer 214 from a heater apparatus 220. The heater apparatus 220 is used to heat the water layer 214 to aid in the generation of water vapour 216 for the gas flow 210 (e.g., heater heats water layer to at least 100° C. to produce water vapour). A detailed description of the heater apparatus 220 is given below.

The function of the water distribution member 211 (including the first compartment wall 212, the water layer 214, and the second compartment wall 218) is to distribute water to the gas passage layer 213.

The humidifier apparatus 110 has a base plate 222 which fits into the housing 112, by being received within a downwardly extending peripheral flange 126 of the housing 112. When the base plate 222 is fully inserted into the base of the housing 112, the base plate 222 abuts against the periphery of the second compartment wall 218 and against a shoulder 224 of the housing 112. In this position, the base plate 222 provides support to the water layer 214 via the second compartment wall 218 and provides a gas seal to the gas flow path 210. The base plate 222 also provides support to the heater apparatus 220. A flexible ridge 226 which is part of or joins the flange 126 aids in securing the base plate 222 against the shoulder 224 of the housing 112. In alternative embodiments, the securing function of the ridge 226 may replaced by conventional securing rings, pins, screws or other fastening devices for securing as commonly used by those skilled in the art.

The gas passage layer 213 may have by way of example breadth and length dimensions of about 50 to 150 mm respectively, e.g., about 100 by 100 mm. The thickness of the gas passage layer 213 above the first compartment wall 212 may be in the range of about 2 to 20 mm, e.g., about 5 to 15 mm (e.g., about 10 mm). The housing 112 with the first compartment wall 212 defines a gas volume in the humidifier apparatus 110 of about 50 to 500 ml, e.g., about 50 to 250 ml (e.g., about 80-150 ml). As described above, the dimensions and capacities given here and later are given by way as examples for the embodiments described. Other dimensions and capacities to those given may be used.

Figure 3:
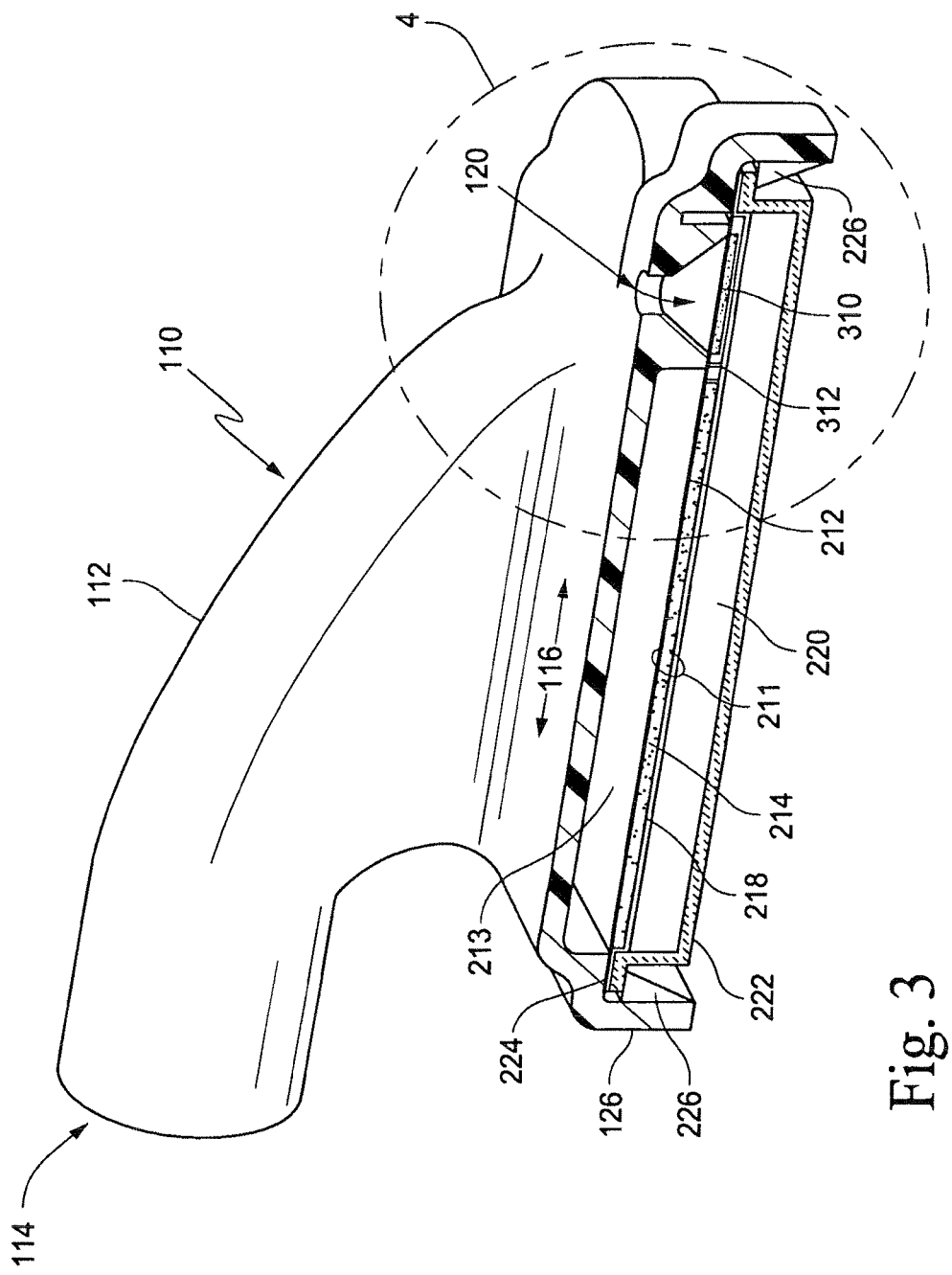
FIG. 3 is a cross-sectional view taken along the line 3-3 of FIG. 1.

FIG. 3 is a cut away view taken along line 3-3 in FIG. 1. FIG. 3 shows further internal components within the humidifier apparatus 110 and in particular the water distribution member 211.

Figure 4:
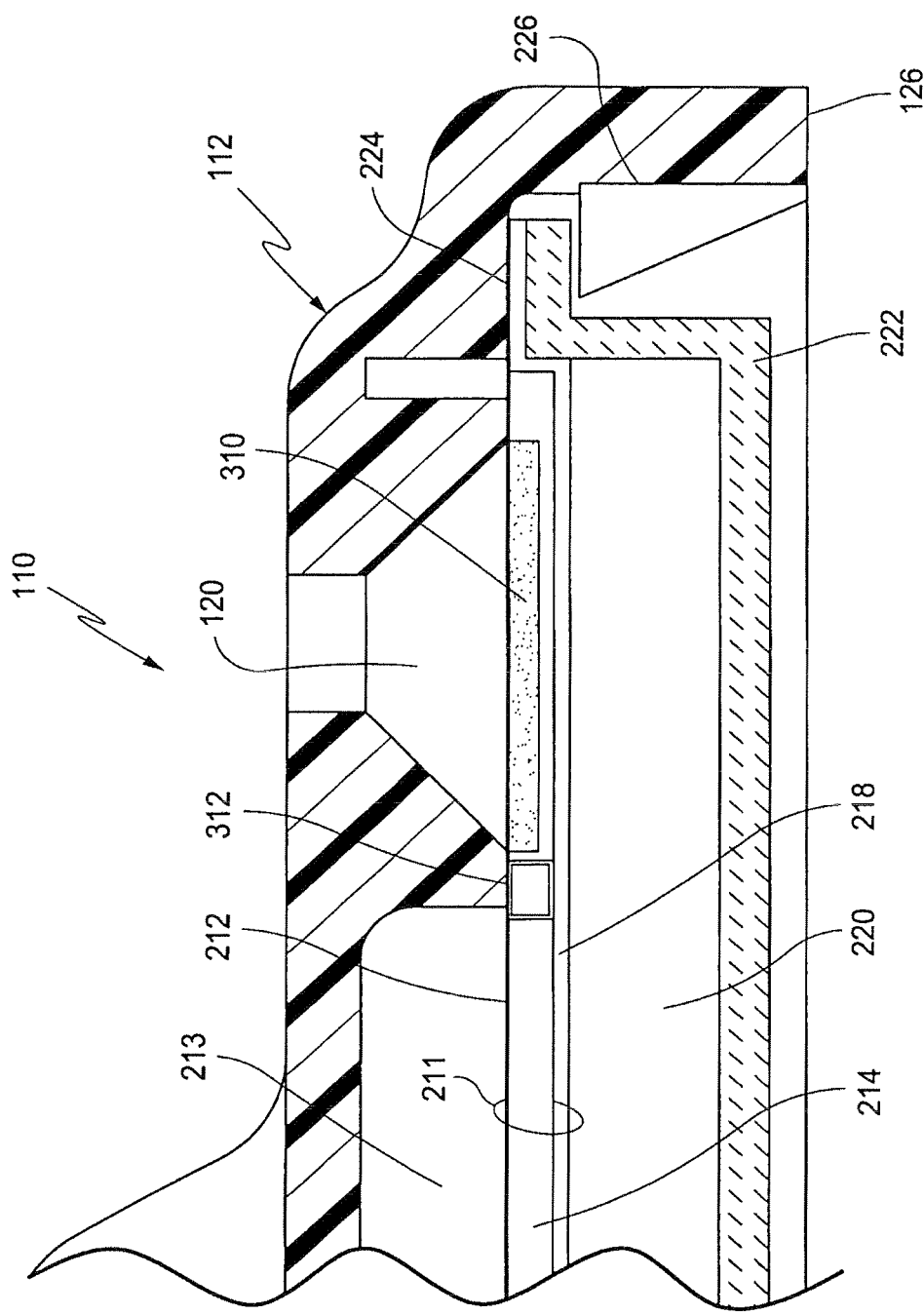
FIG. 4 is an enlarged view of the circled region 4 in FIG. 3.

FIG. 4 is an enlarged view of the circled region 4 in FIG. 3. As illustrated, liquid water to replenish the water layer 214 passes into the humidifier apparatus 110 via the water inlet passage 120 which increases in its transverse cross-section in order to distribute water across a filter 310 within the water distribution member 211. In an embodiment, the lower section of the water inlet passage 120 is conical. The water inlet passage 120 volume above the filter 310 may also serve as a small reservoir of water for the water layer 214. The filter 310 performs as a sterile filter to produce sterile water that may drain into the water layer 214 via a water inlet 312 that is within the water distribution member 211. A filter to produce sterile water by removing bacterial and viral disease causing agents may also remove other agents, such as algae and fungal spores, which may lead to the growth of undesirable agents in the warm and moist environment within the humidifier apparatus 110. In an alternate embodiment, the filter may remove particulates and/or dissolved ions from the liquid water to prevent fouling and blockages of the humidifier apparatus 110 in use. In a further embodiment, the filter 310 may be in the form of a plug which also occupies the conical space of the water inlet passage 120 that is above the first embodiment of the filter 310. In another alternate embodiment, the filter 310 may be omitted from the water distribution member 211 and the water inlet passage 120 so that the water travels directly from the water inlet passage 120 to the water inlet 312.

Further embodiments of the water distribution member 211 are described below with reference to FIGS. 6 to 9.

Housing Embodiments

In FIGS. 1 and 2, the gas inlet 114 and gas outlet 118 are located at either end of the length dimension 122 of the humidifier apparatus 110. As illustrated, the gas inlet 114 is shown in a horizontal orientation and the gas outlet 118 is shown in a vertical orientation. However, the location and orientation of the gas inlet 114 and gas outlet 118 may be varied about the humidifier apparatus 110. For example, in an alternate embodiment the gas inlet and outlet 114, 118 may be attached at either end of the breadth dimension 124 of the humidifier apparatus 110. Or, in another embodiment, the gas inlet and outlet 114, 118 may be attached opposite each other with respect to the length dimension 122 or breadth dimension 124 but with a similar orientation to the horizontal/vertical. In an embodiment, the positioning of the gas inlet and outlets 114, 118 is such that they may be opposed to each other across the gas passage layer 213 in order to maximise the amount of water vapour 216 taken up by the gas flow 210 across the water distribution member 211. As an alternative, the gas inlet and outlets may be adjacent to one another with the gas passage layer extending along a tortuous path or a smaller path sufficient for humidification. Thus, any position for the gas inlet and outlets 114, 118 serving this principle may be appropriate.

In yet another embodiment of the housing 112, the generally rectangular plan view shape of the housing may be of any suitable shape. For example, the plan view shape of the housing may be circular or elliptical.

In the corresponding embodiments to the housing 112, the gas passage layer 213, with respect to FIGS. 2 to 5, may be any suitable dimensions or shape to suit the housing 112 embodiments as described above. Similarly, the water distribution member 211 embodiments, with respect to FIGS. 2 to 10, may have dimensions and shapes to suit the housing 112 embodiments as described above.

Removable and Replaceable Fittings

Figure 5:
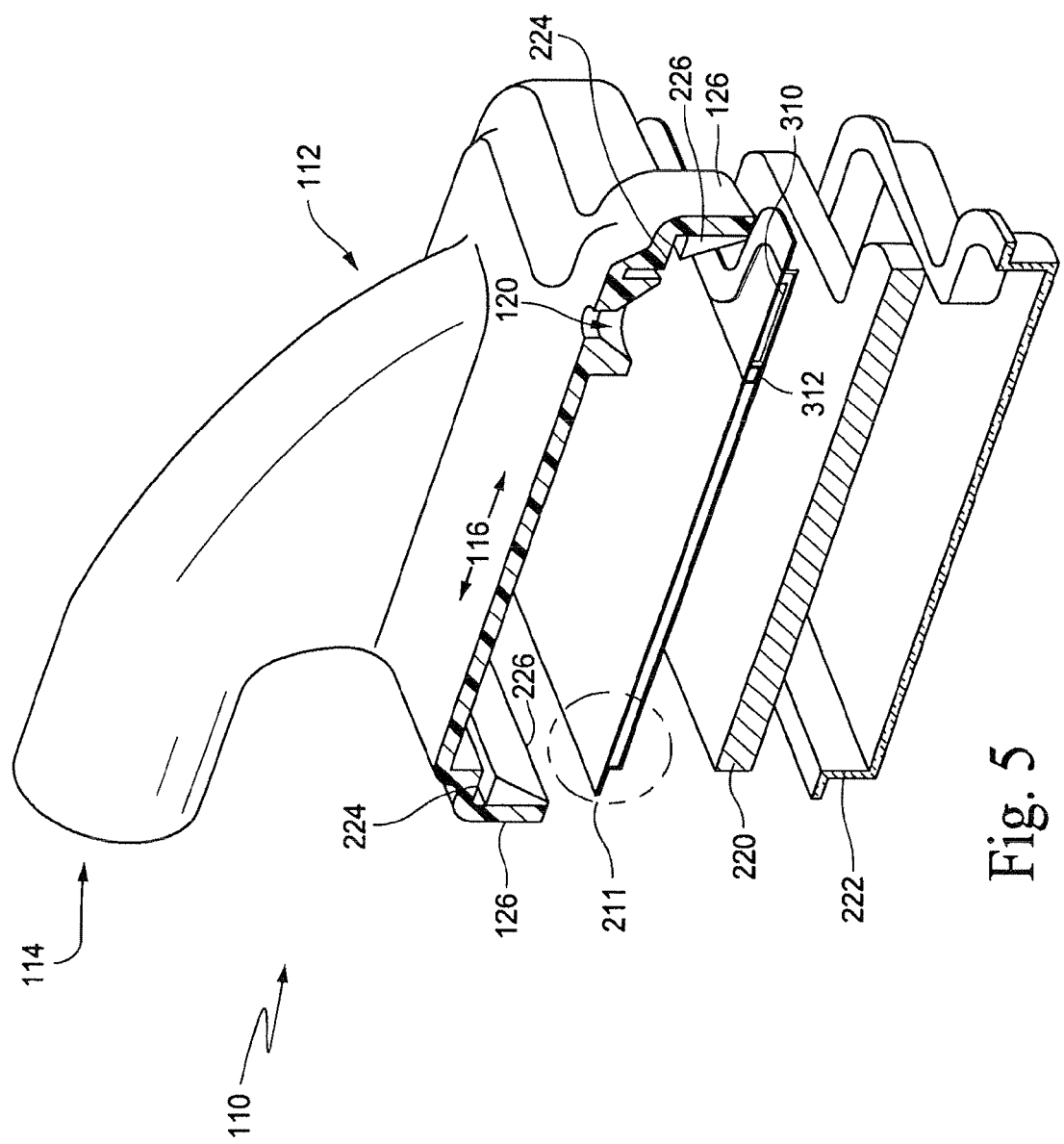
FIG. 5 is an exploded view of FIG. 3.

FIG. 5 is an exploded version of FIG. 3. FIG. 5 schematically illustrates the various components of the humidifier apparatus 110 which can be readily disassembled and re-assembled. The base plate 222 may be separated entirely and then readily re-attached to the housing 112. The base plate 222 is released from the housing 112 by bending back the flexible flange 126 so that the protruding edge of the ridge 226 no longer secures the periphery of the base plate 222 to the shoulder 224. The base plate 222 may then be re-installed into the base of the housing 112 by a simple press fit to negotiate the base plate's 222 peripheral edge past the flexible ridge 226.

When the base plate 222 is removed from the base of the housing 112, the heater apparatus 220 which is seated in the base plate 222 may be removed and replaced or serviced. In addition, the water distribution member 211 may be removed from the housing 112 and replaced as a disposable item or serviced and replaced as described below.

In another embodiment, the heater apparatus 220 and base plate 222 are not separable from each other and form a single component.

When the components described above are removed from the housing 112, the internal surfaces of the housing 112 may be readily accessed for inspection, cleaning or replacing as a disposable item. The water distribution member 211 may also be inspected, cleaned and sterilised or replaced as a low cost disposable item. The heater apparatus 220 and base plate 222 may be more durable and higher cost components which may be designed to be re-useable many times, although alternate embodiments are described below for the heater apparatus 220 and base plate 222 that are low cost and disposable.

The ability of the humidifier apparatus to be readily disassembled and re-assembled with replaceable components as described above is of a particular advantage for the on-going ease of maintenance of the humidifier apparatus 110 by a patient or their carer during the use of the respiratory apparatus.

The humidifier apparatus 110 may be readily used by different patients by attention to the components that are liable to contamination in use. For example, the housing 112 and the water distribution member 211 may be readily cleaned and sterilised or simply replaced as disposable items. The base plate 222 and heater apparatus 220 may not be contaminated because they are generally not in contact with the patient or the patient's airway with its associated secretions. Consequently, the base plate 222 and heater apparatus 220 may be re-used.

Water Distribution Member Embodiments

Figure 6:
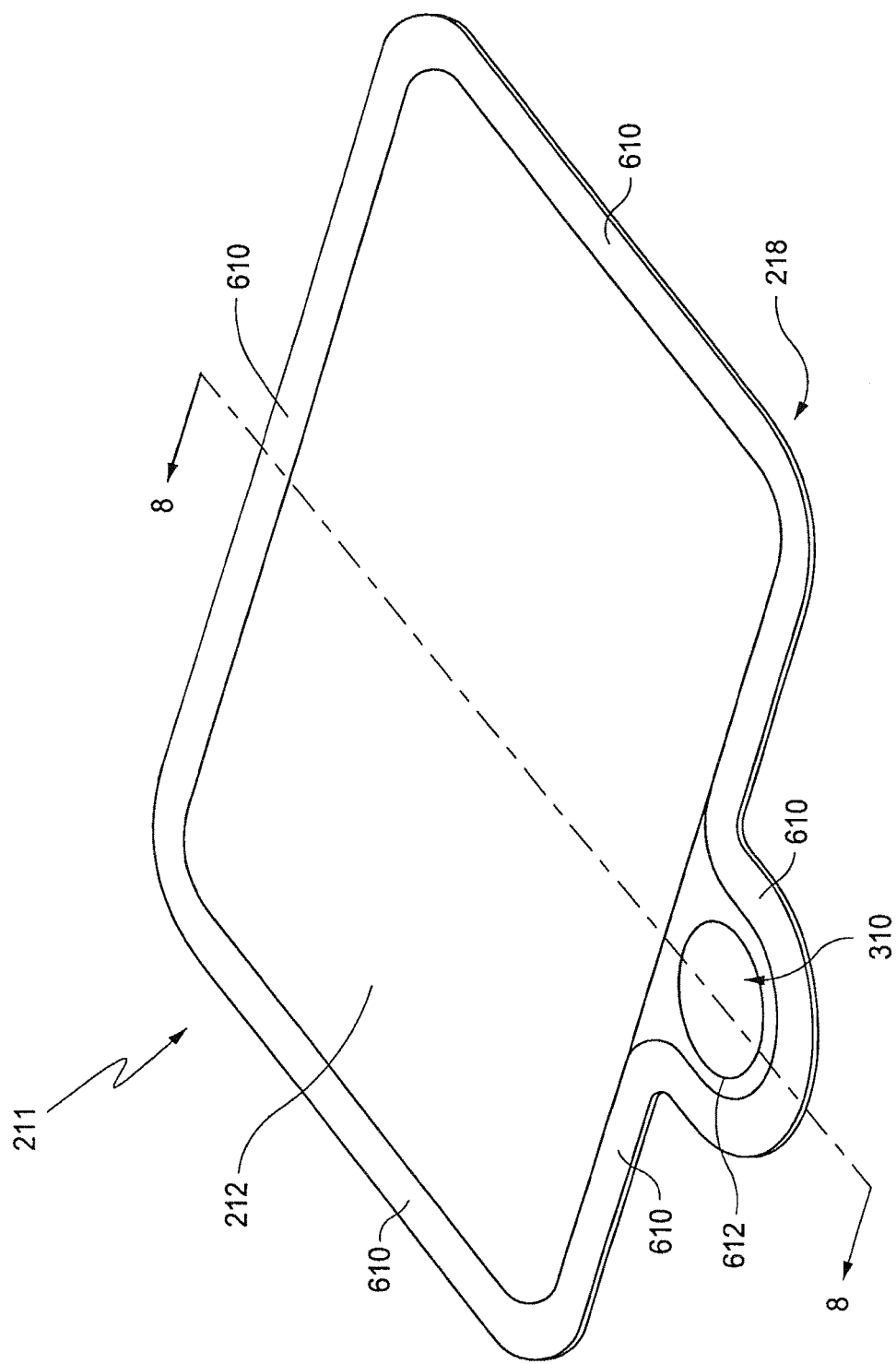
FIG. 6 is a schematic perspective view of a water distribution member according to an embodiment of the present invention.

FIG. 6 is a perspective view of the water distribution member 211. The plane surface of the first compartment wall 212 is shown uppermost with it extending to the shoulder 224 of the housing 112. The first compartment wall by way of example may have breadth and length dimensions of about 50 to 150 mm respectively, e.g., about 100 by 100 mm. The overall dimensions and shape of the water distribution member 211 may correspond to that of the gas passage layer 213 and the housing 112 embodiments described above.

The first compartment wall 212 is preferably a semi-permeable membrane with the characteristic of preferentially allowing water vapour 216 to pass through it but impeding liquid water so that the gas passage layer receives water vapour 216 but no liquid water from the water layer 214.

The semi-permeable membrane may be formed of a material which has fine pores or perforations and may also be hydrophobic, the fineness of the porosity or the perforations and/or the degree of hydrophobicity being adapted to result in the desired effect of semi-permeability for this application.

Some examples of semi-permeable membrane materials with suitable characteristics for use in the water distribution member according to an embodiment of the present invention include:

Porous polytetrafluroethylene (PTFE) materials, microporous PTFE membranes and expanded PTFE (ePTFE) from Gore-Tex®, W.L. Gore & Associates, Inc of Maryland USA.

Tyvek® spun polyethylene sheet material from DuPont.

PTFE mesh sold as Fluorcarbon SPECTRA/MESH® by Spectrum Laboratories of Rancho Dominguez, Calif. USA.

Fibrous membranes consisting of auxetic fibres (fibres with a negative Poisson's Ratio).

A more comprehensive discussion of suitable semi-permeable membrane materials is included in Patent Application No. WO 2006/069415 A1 "Respiratory Mask having Gas Washout Vent and Gas Washout Vent Assembly for Respiratory Mask", the contents of which are incorporated herein by reference.

In another embodiment, the surface of the first compartment wall 212 may have dimples or corrugations formed within it so as to increase the area of interaction with the gas flow path 210 and/or to promote the turbulent mixing of the water vapour 216 with the gas flow path 210.

The first compartment wall 212 is joined to the second compartment wall 218 by a bonding strip 610 about the periphery of both compartment walls 212, 218 to form a thin envelope containing the water layer 214. The bonding strip 610 between the first and second compartment walls 212, 218 may be achieved by heat sealing, an adhesive, welding or any suitable method of manufacture.

In FIG. 6, the filter 310 is visible thru a filter aperture 612. The filter 310 is sandwiched at its periphery by the first and second compartment walls 212, 218 which in turn are bounded by the bond strip 610. Liquid water flows through the filter aperture 612, the filter 310 and into the water layer 214 (not shown in FIG. 6) of the water distribution member 211.

The second compartment wall 218 on the underside of the water distribution member 211 shown in FIG. 6 may be formed of materials of the type and form suitable to conduct heat from the heater apparatus 220 into the water layer 214. Desirable properties of the second compartment wall 218 include that it may be thin so as to conduct and dissipate heat rapidly with very low thermal inertia and structurally robust and flexible so that it may readily conform to the surface of the heater apparatus 220. Suitable materials for the second compartment wall 218 may be metallized plastic film, a metal foil such as aluminium or metal plastic composite. Further embodiments of the second compartment wall 218 in combination with the heater apparatus 220 are described below with the heater apparatus 220 description.

A thin envelope configuration as described above for the water distribution member 211 enables the water layer 214 within to be thin. In an embodiment, the thickness of the liquid water layer 214 by way of example may be about 1-5 mm, e.g., less than about 2 mm, however larger capacity versions may have a thickness up to and greater than 10 mm. The corresponding volume of the water layer 214, by way of example, may range from less than 10 ml to larger capacity versions that may be up to and greater than 150 ml.

A thin water layer 214 of low volume may be heated rapidly with modest heating to produce adequate water vapour 216 for the humidification of the gas flow path 210. Modest heating requirements enable a heating apparatus 220 of low power requirements to be used in the humidifier apparatus 110.

In use, water vapour may also be produced within the envelope of the first and second compartment walls 212, 218 as a result of heating from the heater apparatus 220. In situations where a high humidification rate is required within the gas flow path 210, the rate of heating by the heater apparatus 220 may be such that considerable amounts of water vapour are present with the liquid water within the water layer 214.

An alternate embodiment of the water distribution member 211 may include the use of additional, partial bonding strips (not shown) across the plane of the first and second compartment walls 212, 218 that partially join the compartment walls 212, 218. The additional, partial bonding strips may be arranged in such a manner to improve the rigidity of the water distribution member 211, allow water to flow through the water layer 214 and to prevent ballooning where the envelope of the first and second compartment walls 212, 218 may be inflated by the supply of water at an excessive pressure or vigorous heating by the heater apparatus 220 generating excessive water vapour. Ballooning of the envelope of the first and second compartment walls 212, 218 may obstruct the gas passage layer 213.

Filter Composite Structure

Figure 7:
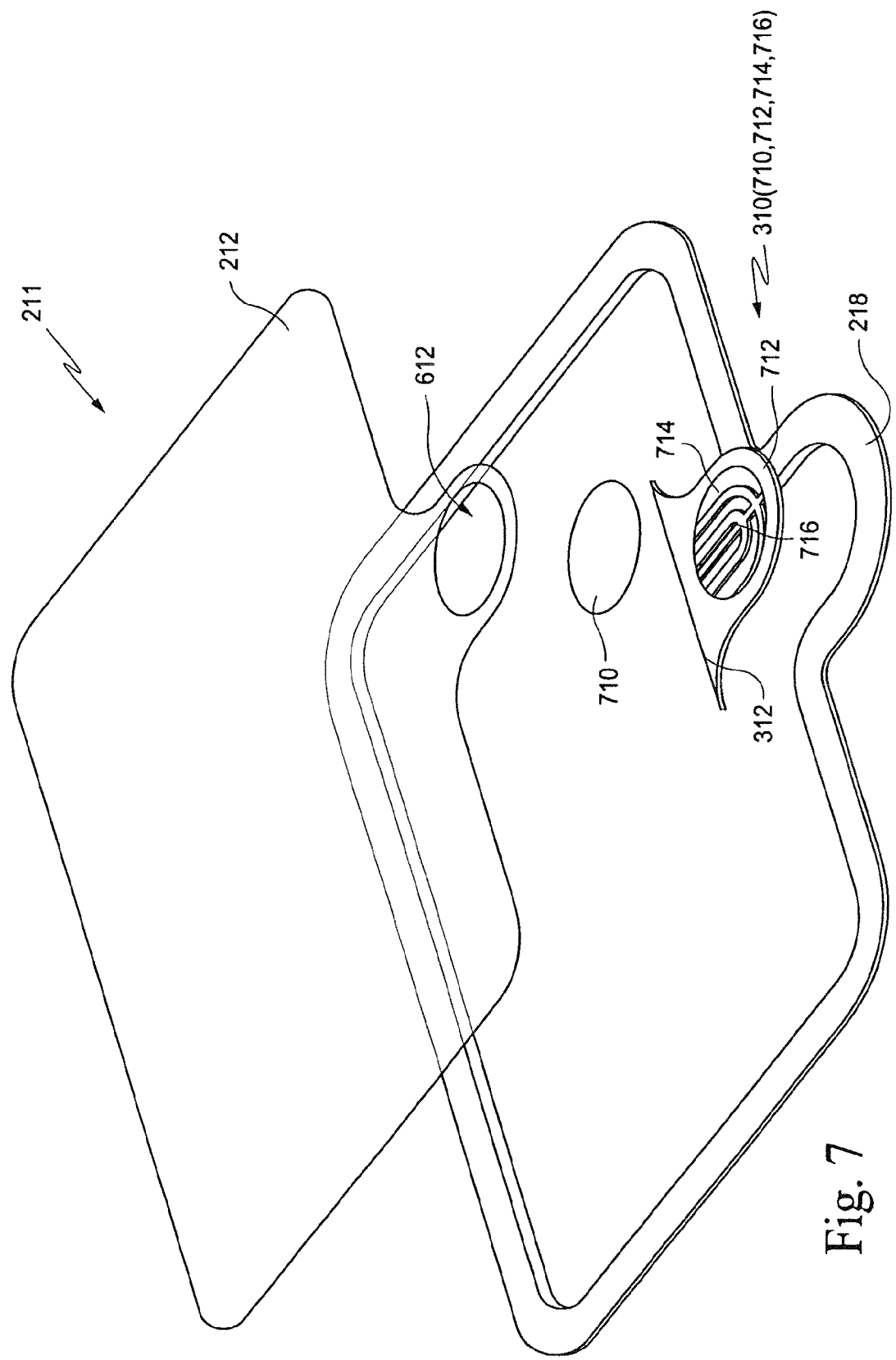
FIG. 7 is an exploded view of FIG. 6.

FIG. 7 is an exploded perspective view of the water distribution member 211 with an alternative embodiment of the filter 310 to that described with reference to FIG. 3 above. In this embodiment, the filter is in the form of a composite filter comprising a filter disc 710 and a filter support 712. The filter disc 710 performs the filtering functions described above for the other embodiments. The filter disc 710 sits below the filter aperture 612 so as to receive all the water from the water inlet passage 120. The filter disc 710 is supported by and sits within the filter support 712 in a manner that allows the water from the water inlet passage 120 to pass through the thickness of the filter disc 710 and freely drain from the lower side of the filter disc 710 to the water inlet 312. To allow the free draining of the filter disc 710, the filter support 712 consists of a very porous material which allows the filtered water to pass freely through it whilst providing structural support to the filter disc 710. The filter support 712 material may be any one of many suitable porous materials such as foam plastics or foam form metals which are approved for medical respiratory apparatus use or alternatively a suitable plate with many through holes or a plate with many, small, raised protrusions on its surface. To aid in the free draining function of the filter support 712, ribs 714 are located below the filter disc 710. The ribs 714 form rib channels 716 which allow the filtered water to proceed freely to the water inlet 312 through the filter support 712 portion adjoining the water inlet 312.

An advantage of the filter composite structure 710, 712, 714, 716 described above is that the expensive filtering material is limited to a filter disc 710 to coincide with the filter aperture 612 rather than occupying the rest of the filter volume in which the filter support 712 resides.

Figure 8:
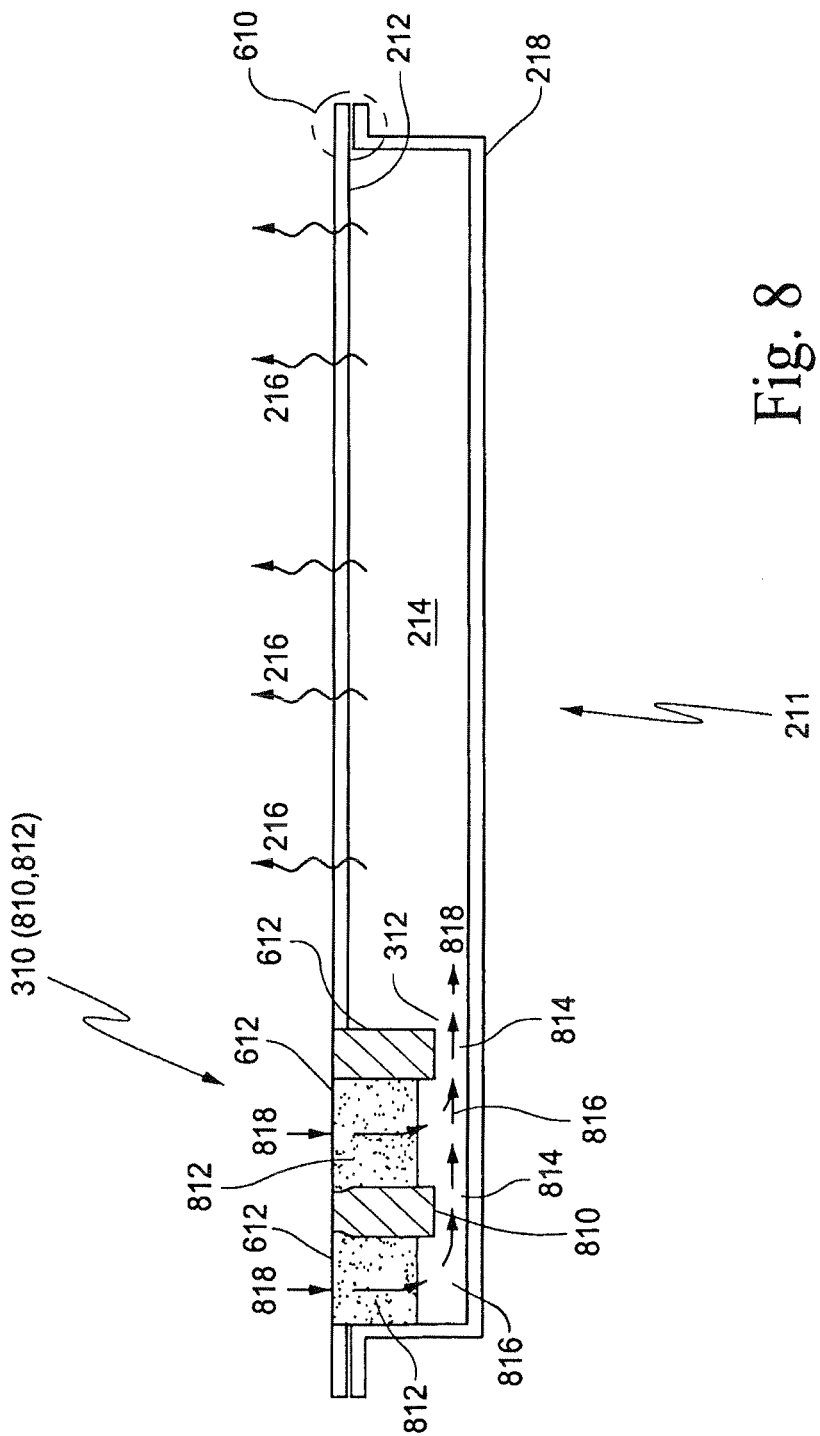
FIG. 8 is a cross-sectional view across the line 8-8 of FIG. 6 of an alternate embodiment of a composite filter structure.

FIG. 8 is a cross-sectional view across the line 8-8 of FIG. 6 of an alternate embodiment of a composite filter structure. In this embodiment, multiple filter walls 810 are used to support a filter infill 812 where the filter infill 812 performs the filtering functions described above for the other filter embodiments. The top of the filter infill 812 corresponds to the filter aperture 612 for receiving the water for filtering. Along the bottom of each of the multiple filter walls 810 are a number of filter wall apertures 814 that allow the filtered water to move from and through a number of bottom channels 816 (which are below the filter infill 812) to the water inlet 312 of the water layer 214. In use, the water flow 818 is indicated by the dashed lines with arrows. For this embodiment, there may be multiple water inlets 312 depending on the number of filter wall apertures 814 in the filter wall 810 adjoining the water layer 214.

In an alternative embodiment to those described above, the filter 310, 710, 712, 714, 716, 810, 812 may be omitted and/or optional. In this embodiment, the liquid water may pass freely through the filter aperture 612, through the water inlet 312 and into the water layer 214 as bounded by the first and second compartment walls 212, 218.

Chassis for Water Distribution Member

The single structure form of the water distribution member 211 facilitates it being readily removable from the humidifier apparatus 110 and being replaceable as described above with reference to FIG. 5 and below with reference to FIGS. 9 and 10.

Figure 9:
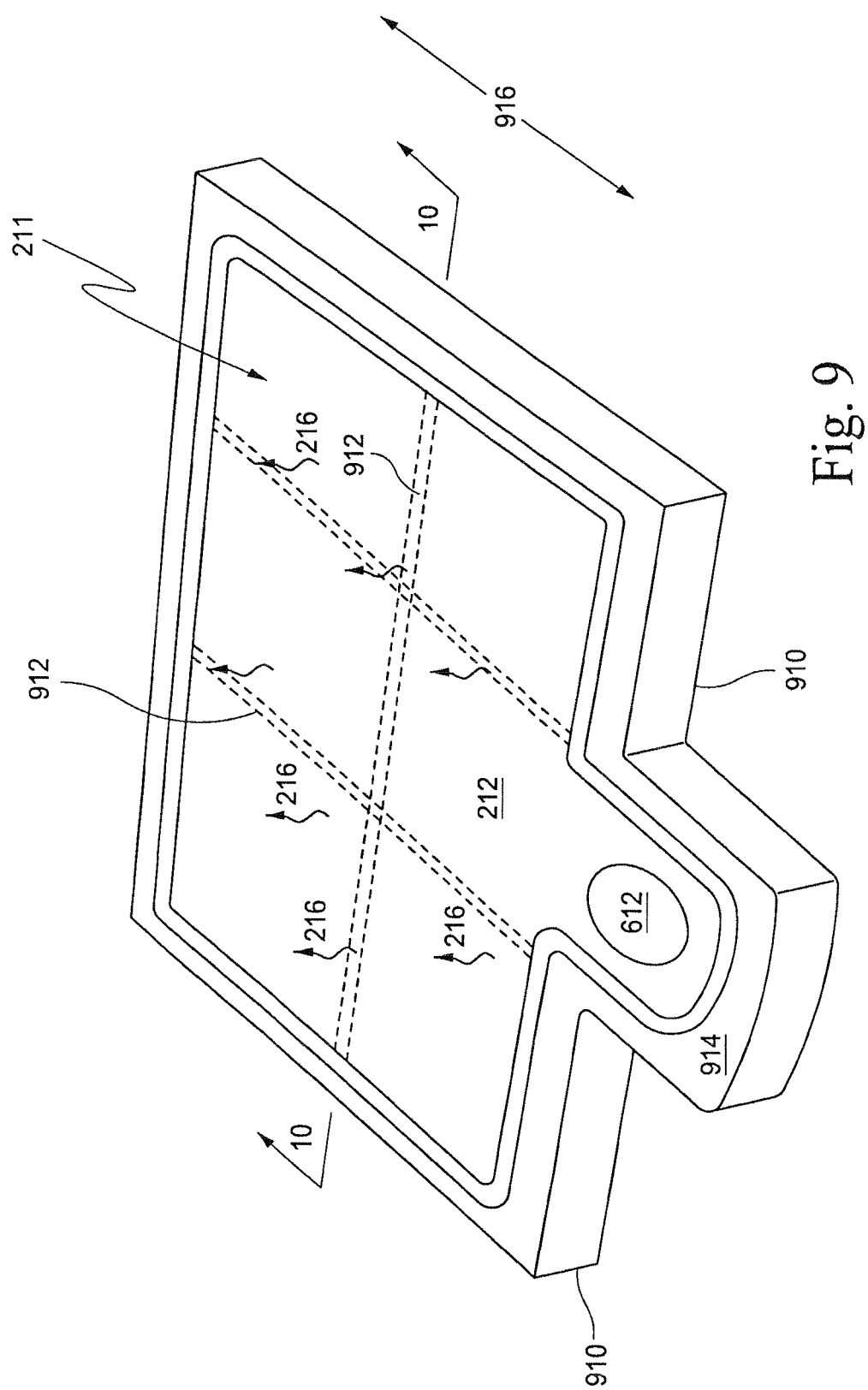
FIG. 9 is a schematic perspective view of a chassis for the water distribution member of FIG. 6 according to an embodiment of the present invention.

FIG. 9 is a perspective view of a chassis 910 that may be used as a further embodiment for the support of the water distribution member 211 according to any one of the water distribution member 211 embodiments described above. The chassis 910 may be made of a material which is rigid, such as plastic or a metal frame. To improve the rigidity of the chassis 910, braces 912 may be incorporated in the underside of the chassis 910. The braces 912 are shown in dashed outline on FIG. 9 in order to represent their location under the water distribution member 211. The braces 912 are of a thin profile and of an appropriate material for contact with the heater apparatus 220.

The chassis 910 may have a protruding tab 914 that facilitates the insertion and removal of the chassis 910 and water distribution member 211 to the humidifier apparatus in the direction shown by the bi-directional arrow 916. The arrangement (not shown) for accommodating the chassis 910 into the humidifier apparatus 110 may comprise of increasing the downward length of the flange 126 and increasing the distance between the shoulder 224 of the housing 112 and the periphery of the base plate 222 in order to allow the chassis to slid in and out of a space between the shoulder 224 and the base plate 222. In order for the chassis 910 to access this space, the flange 126 along the length dimension 122 may be omitted. In addition, the profile of the chassis 910 may be adapted so that as it slides into the humidifier apparatus 110 the periphery of the water distribution member 211 is caused to make a gas tight seal with the shoulder 224 of the housing 112. Similarly, the second compartment wall 218 of the water distribution member 211 is caused to be in thermal contact with the heater apparatus 220.

The chassis 910 may be secured in position within the humidifier apparatus 110 by any one of many mechanical options available to a person skilled in the art.

Figure 10:
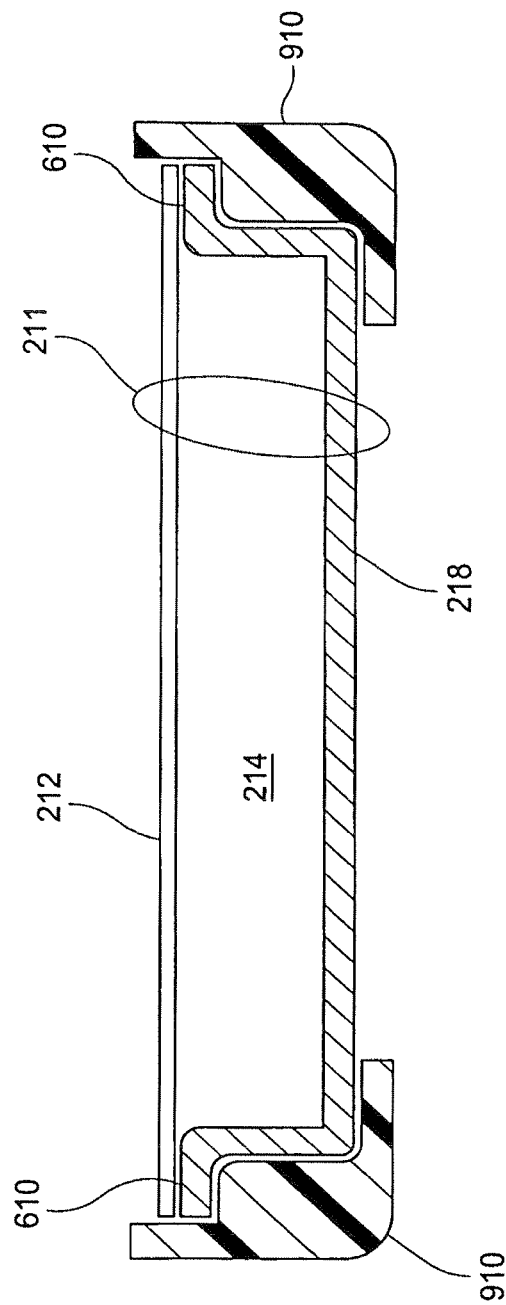
FIG. 10 is a cross-sectional view along the line 10-10 of FIG. 9.

FIG. 10 is a cross-sectional view along the line 10-10 of FIG. 9. FIG. 10 illustrates how the water distribution member 211 is contained within the chassis 910. The water distribution member 211 may simply rest within the chassis 910.

The advantage of an alternate embodiment including a chassis 910 is that a simple single step sliding action to replace the water distribution member 211 may be done rather than a more involved action of the removal of the base plate 222 and the heater apparatus 220 as described in other embodiments above.

In another embodiment, the humidifier may have a hinged upper section to allow access to the water distribution member for easy insertion and replacement.

Wick Embodiment

An alternative embodiment for the water distribution member 211 is the use of a wick and/or capillary action device (not shown) in place of the first compartment wall 212 and the water layer 214. The wick device has the ability to conduct water upon or within the wick device such that water is available for vaporisation into the gas passage layer 213. In addition, a capillary action may also be involved within the wick device. An example of a suitable wick device is a material which is hydrophilic so that the water has a tendency to spread across the extent of the material. Materials that may be suitable include cotton, activated perfluorinated polymer (e.g., "NAFION" stabilised perfluorosulfonic acid/PTFE copolymer by DuPont), polyester copolymer (e.g. SYMPATEX polyester/polyether copolymer by Sympatex Technologies GmbH of Germany) and polyester fabrics (e.g., COOLMAX polyester fabrics by Invista of USA). Alternatively, a material may be imparted hydrophilic characteristics by using a particular liquid film or the application of a gel or solid film.

The wick device may have an internal structural form of a fabric, sponge, a film, a bundle of fibres or a hydrophilic porous, flexible solid, e.g., plastic, metal or ceramic. The external form of the wick device may be of a continuous liner upon the second compartment wall 218. In an alternate embodiment of the external form, the wick device liner may be in the form of a corrugated or dimpled liner upon the second compartment wall 218 so that the area of interaction between the gas flow path 210 and the wick device is increased.

Alternatively, the wick device may be in the form of a very gas porous membrane that may extend partially or wholly across the transverse cross section of the gas passage layer 213, the material forming the membrane being as per that described above for the wick.

In another embodiment of the wick device, the second compartment wall 218 may be omitted and the wick device as a continuous sheet may be joined to a peripheral frame in place of the bond strip 610 described in the above embodiments. In a further embodiment, a grid support structure may be located with the continuous sheet of the wick device and also be joined to the peripheral frame.

The water supply for the wick device may be in the forms described above for the other embodiments of the water distribution member 211.

In a further hybrid embodiment of the water distribution member 211, the wick device may reside within the envelope formed by the compartment walls 212, 218, as described above for the other embodiments.

Heater

For all the above described embodiments of the water distribution member 211, a heater apparatus 220 may be used to increase the amount of water vapour 216 produced by the water distribution member 211. The heater apparatus 220 may consist of a heating element (not shown) embedded within or attached to a metal or ceramic block which is against the second compartment wall 218. The heating element may for example consist of a resistive conductor. The conductor may consist of multiple resistive conductors connected to each other in series, parallel or segmented about the heater apparatus 220 in order to allow uniform, variable and/or sectional heating of the second compartment wall 218 and through it the water layer 214.

The base plate 222, as well as providing support as described above, insulates the heater apparatus from any surface that the humidifier apparatus 110 may rest upon. The base plate 222 may be made of a material or a composite of materials which provide suitable refractory properties for the temperature range of the heater apparatus 220 and suitable insulation properties. A person skilled in the art of manufacture may select from any one of many widely available materials suitable for the purpose, for example a ceramic composite or a variety of high temperature plastics.

In addition, the base plate 222 may have electrical connections (not shown) to which the heating element of the heater apparatus 220 may connect with in a manner that allows the base plate 222 to be readily disassembled and re-assembled to the heater apparatus 220 as described above with reference to FIG. 5. The external surface of the base plate 222 may have corresponding electrical connections (not shown) so that the heating element may receive its electrical power supply from the respiratory apparatus that the humidifier apparatus 220 may be connected with or alternatively the heating apparatus may have its own power supply. The form and materials that may be used for the electrical connections may be any suitable one of the many options available to a person skilled in the art. For example, the metal electrical contacts may be of a male-female engagement arrangement or a simple, flat sliding contact.

In an alternative embodiment, the heater apparatus 220 may be located within a section of the respiratory apparatus that the humidifier apparatus 110 sits upon. The heater apparatus 220 may have a heater plate (not shown) which may be in thermal contact with the base plate 222 when the humidifier apparatus 110 rests upon the respiratory apparatus. The base plate 222 in this embodiment is of a suitably thermally conductive material, such as a metal, which is also in thermal contact with the second compartment wall 218.

In a further embodiment, the base plate 222 and the second compartment wall 218 may be combined in a single structure to form a heater plate that may be comprised of thin metallised foil in the portion adjacent to the water layer 214. A peripheral support rim for the heater plate 218, 222 may be used to secure the water distribution member 211 against the shoulder 224 with the ridge 226.

Filament or Strip Heater

In another embodiment, the heater apparatus 220 may be in the form of a filament or tape heater element which may be attached to the side of the base plate 222 which is adjacent to the second compartment wall 218. In an alternative embodiment, the filament or tape heater element may be attached to or incorporated within the second compartment wall 218. In yet another embodiment, the filament or tape heater element may be located within the water layer 214 or in the wick device embodiment of the water distribution member 211 the heater element may be interwoven with or adjacent to the wick device as described above. The necessary electrical connections to the electrical power supply are as described above.

The filament heater element may be in the form of a conventional resistive wire heater. The tape heater element may be a flexible tape heater as described in Australian Patent Application No. 2006906224 "Humidifier for a Respiratory Apparatus", the contents of which are incorporated herein by reference. In one embodiment of the flexible tape heater, the heating element may be formed by printed circuit techniques applied to a surface of a flexible substrate such as silicone rubber, all-polyimide or PTFE. Included in the printed circuit techniques which may be used are etched foil, printing and vacuum deposition techniques. The Thermofoil™ range of the type of flexible heaters by Minco of Minneapolis USA, described at www.minco.com, are examples of commercially available strip heaters which may be modified for use in the present application. Alternatively, the flexible tape heater may be formed as a heating element, for example in the form of a resistive wire or ribbon, laminated between tapes of polycarbonate or other suitable plastics film.

Induction Heater

An alternate embodiment of the heater apparatus 220 may comprise of an induction heating system. In such a system, a transmitting induction coil is used to generate electromagnetic radiation which may be transmitted without the requirement for an electrical, magnetic or mechanical connection to an induction receiving element. The electromagnetic radiation induces eddy currents within the induction receiving element which may then heat the heater element by electrical resistance heating (Joule effect). In an alternate embodiment, a design of the induction heating system may use magnetic hysteresis losses for heating in the induction receiving element with or instead of eddy current resistive heating.

Induction heating systems may be designed and fabricated by a person skilled in the art of induction heating systems as well as by reference to novel induction heaters such as in Patent Application No. PCT/AU2007/000274 "Induction Heating System and Method for Humidifier", the contents of which are incorporated herein by reference.

For the humidifier apparatus 110, the transmitting induction coil (not shown) together with the associated power supply and control system may be located with the respiratory apparatus. The humidifier apparatus 220 may be located in the vicinity of the induction coil, sufficiently close that the induction receiving element (not shown) within the humidifier apparatus 220 receives sufficient electromagnetic radiation from the induction coil to induce heating. The induction receiving element may be located between the base plate 222 and the second compartment wall 218 such that it is in thermal communication with the second compartment wall 218. The base plate 222 may be made of materials or of structure to which induction by electromagnetic radiation does not significantly occur. For example, a non-conducting ceramic, plastic or a lamination arrangement of metal and an insulator/dielectric.

In an alternative embodiment, the second compartment wall 218 forms an induction receiving element. The second compartment wall 218 may comprise in part at least of a metal foil that is sufficiently conducting to have eddy currents induced within it and/or sufficiently magnetisable to undergo magnetic hysteresis under the applied electromagnetic radiation. In a further embodiment, the base plate 222 may be omitted.

An induction heating system offers the advantage that the induction receiving element may have a very low thermal inertia such that it may be heated to in excess of 100 degrees Celsius within a short time, for example less than 2 minutes to enable the rapid generation of water vapour 216. Similarly, the low thermal inertia of the induction receiving element enables a rapid cooling down, particularly when the water layer 214 thickness is thin. In addition, for the embodiment where a low cost induction receiving element is incorporated in the second compartment wall 218, the disposability of the water distribution member 211 is improved.

Cooling and Heating by the Heater Apparatus

In a further embodiment to the heater apparatus 220 embodiments described above, the heater apparatus 220 may be a Peltier thermo-electric element that may be used to cool or heat. The Peltier thermo-electric element may be present within the humidifier apparatus 110 or external to it as per the embodiments described above. Electrical supply and control of the Peltier thermo-electric element to heat or cool may be by the respiratory apparatus or a separate electrical supply and control unit.

The Peltier thermo-electric element may be used to cool the water layer 214 to well below the ambient temperature so that the generation of water vapour 216 is minimal and consequently there is minimal humidification of the gas passage layer 213 and the gas flow 210B from the humidifier apparatus 110. Conversely, the Peltier thermo-electric element may be used to variably heat the water layer 214 to produce the desired amount of water vapour 216 to humidify the gas flow 210B from the humidifier apparatus 110.

Sterilisation

In a further embodiment, in-situ high temperature sterilisation may be used with the heater apparatus' 220 capacity to rapidly heat to a temperature in excess of 100 degrees Celsius for a predetermined period of time. The low thermal inertia of the humidifier apparatus 110 allows for its rapid cool down and subsequent use for humidification. Such a sterilising technique offers a convenient method to counteract the lodgement and growth of disease causing agents within the humidifier apparatus 110. An alternative sterilisation method may be by the use of a chemical treatment to one or more surfaces or materials within the humidifier apparatus 110, for example the water distribution member 211 may be permanently impregnated with a chemical that inactivates viruses and arrests bacterial growth.

Humidity Control

Figure 11:
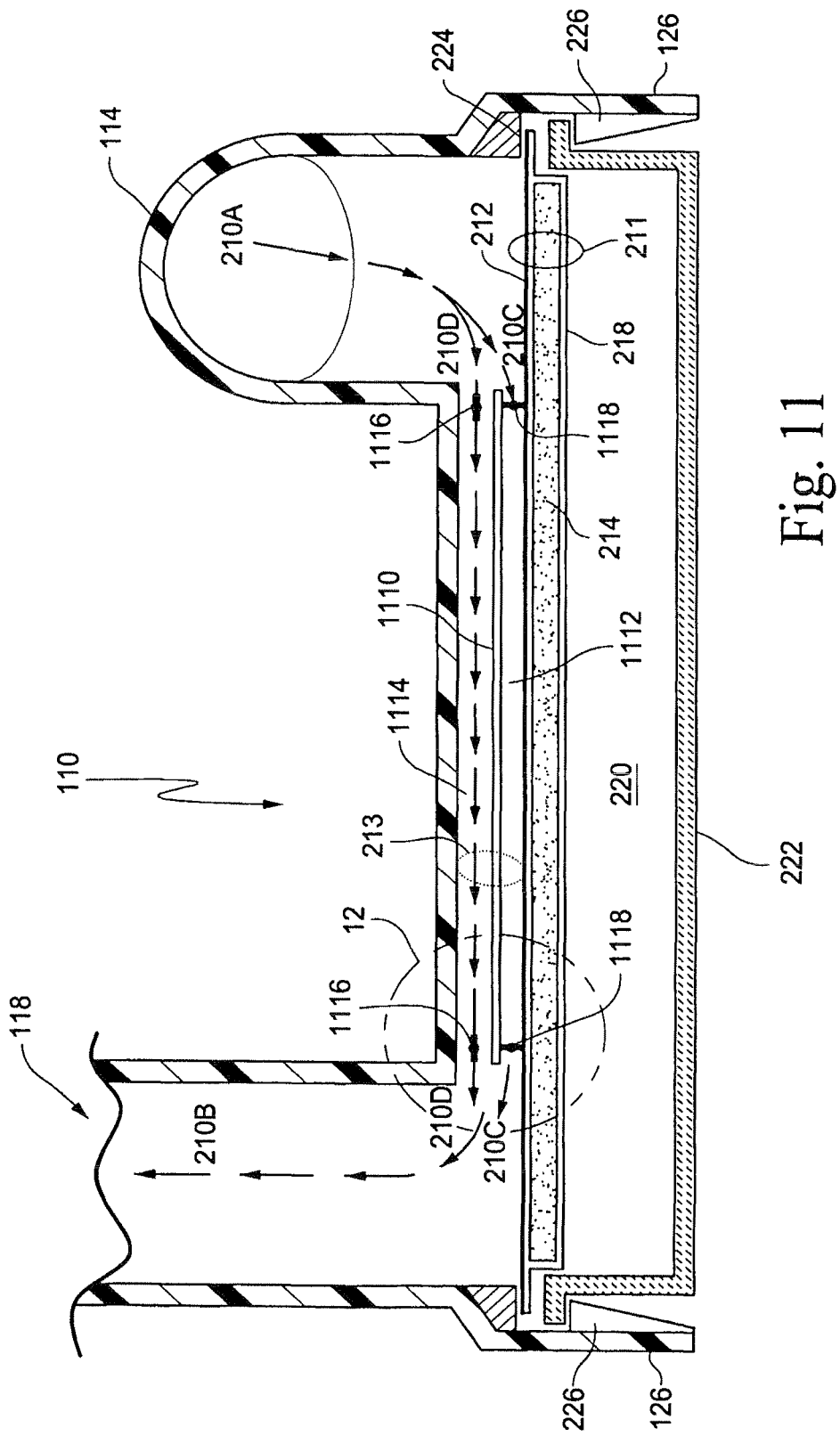
FIG. 11 is an alternate embodiment of the humidifier apparatus in FIG. 2, where devices for humidity control are introduced according to an embodiment of the present invention.

FIG. 11 is a further embodiment of that in FIG. 2 where structures are introduced to enable the amount of humidification of the gas flow path 210 to be controlled. The gas passage layer 213 is vertically split by a plate 1110 into two further passage layers, each for a stream of the divided gas flow path 210A. The humidification gas stream 210C travels in the lower passage layer 1112 along the first compartment wall 212 and may receive water vapour 216 being issued from the first compartment wall 212. The other stream is the dry gas stream 210D which travels along the upper passage layer 1114 and is not humidified. The humidified and dry gas streams are recombined at the exit end of the upper and lower passage layers 1112 and 1114 to form the humidified gas flow 210B which flows out of the humidifier apparatus 110 via the gas outlet 118.

At either end of the upper passage layer 1114 are a pair of miniature upper butterfly valves 1116 which can be used to vary the amount of gas flow 210A entering into the upper passage layer 1114. In FIG. 11 the upper butterfly valves are shown in the open position to allow gas flow 210A to pass freely through as gas flow 210D. The lower passage layer 1112 at either end also has a pair of miniature lower butterfly valves 1118, which in FIG. 11 are shown in the closed position.

Figure 12:
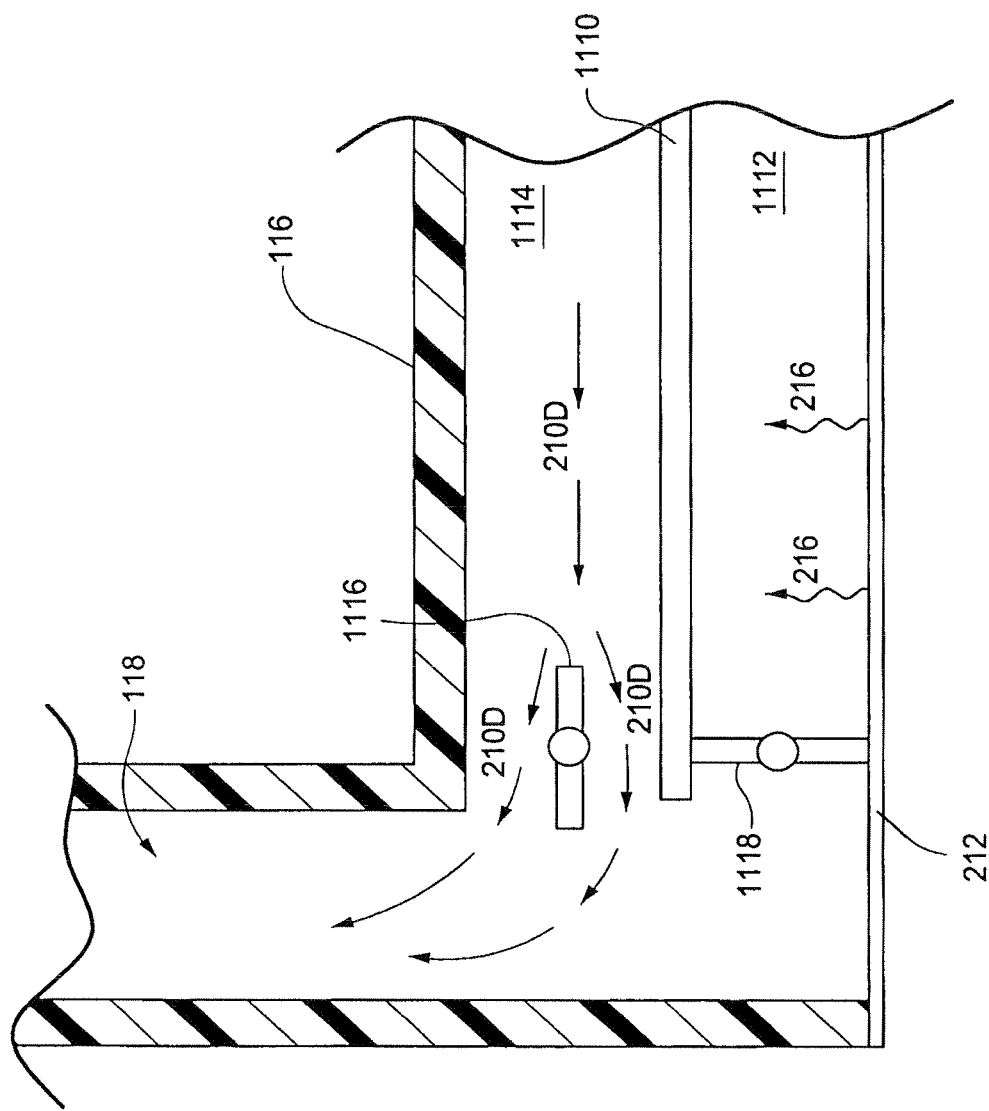
FIG. 12 is an enlarged view of the circled region 12 in FIG. 11.

FIG. 12 is an enlarged view of the dash encircled region 12 in FIG. 11. FIG. 12 illustrates the functioning of the upper and lower butterfly valves 1116, 1118. In this valve configuration, there is no gas flow through lower passage layer 1112 and so no humidification of the gas flow 210 may occur. Only dry gas flow stream 210D may occur. If the pair of lower butterfly valves 1118 are opened fractionally then there will be a humidified gas stream 210C combining with the dry gas stream 210D to form the humidified gas flow 210B. Controlling the relative positions of the upper and lower butterfly valves 1116, 1118 enables the level of humidity in the gas flow path 210B to be varied.

The upper and lower butterfly valves 1116, 1118 may be actuated by any suitable electrical and/or mechanical systems (not shown) available to a person skilled in the art of miniature motion systems. The actuation method may be controlled by a controlling unit (not shown) either located with the respiratory apparatus or as a separate controlling unit. The controlling unit may in turn be controlled by a humidity sensor or humidity controller.

Figure 13:
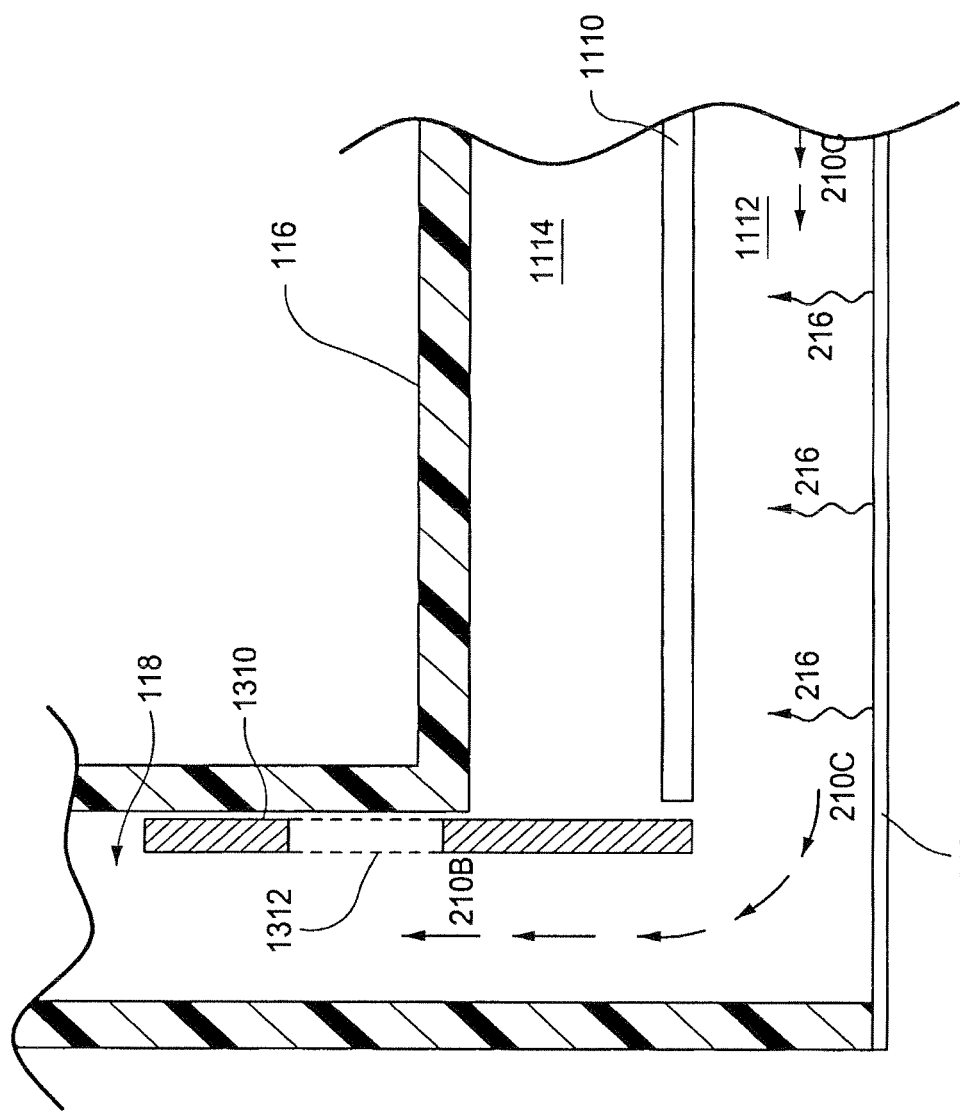
FIG. 13 is an alternate embodiment, to that in FIG. 12, for humidity control.

FIG. 13 is an alternative embodiment to the above butterfly valves, where a sliding shutter 1310 with an aperture 1312 is used to control the relative amounts of the humidified and dry gas streams 210C, 210D. The shutter 1310 position shown in FIG. 13 is obstructing the upper passage layer 1114 at its exit end so that gas flow 210 is preferentially via the lower passage layer 210C. Thus, the ambient gas flow 210A is humidified by its passage through the lower passage layer 210C.

Figure 14:
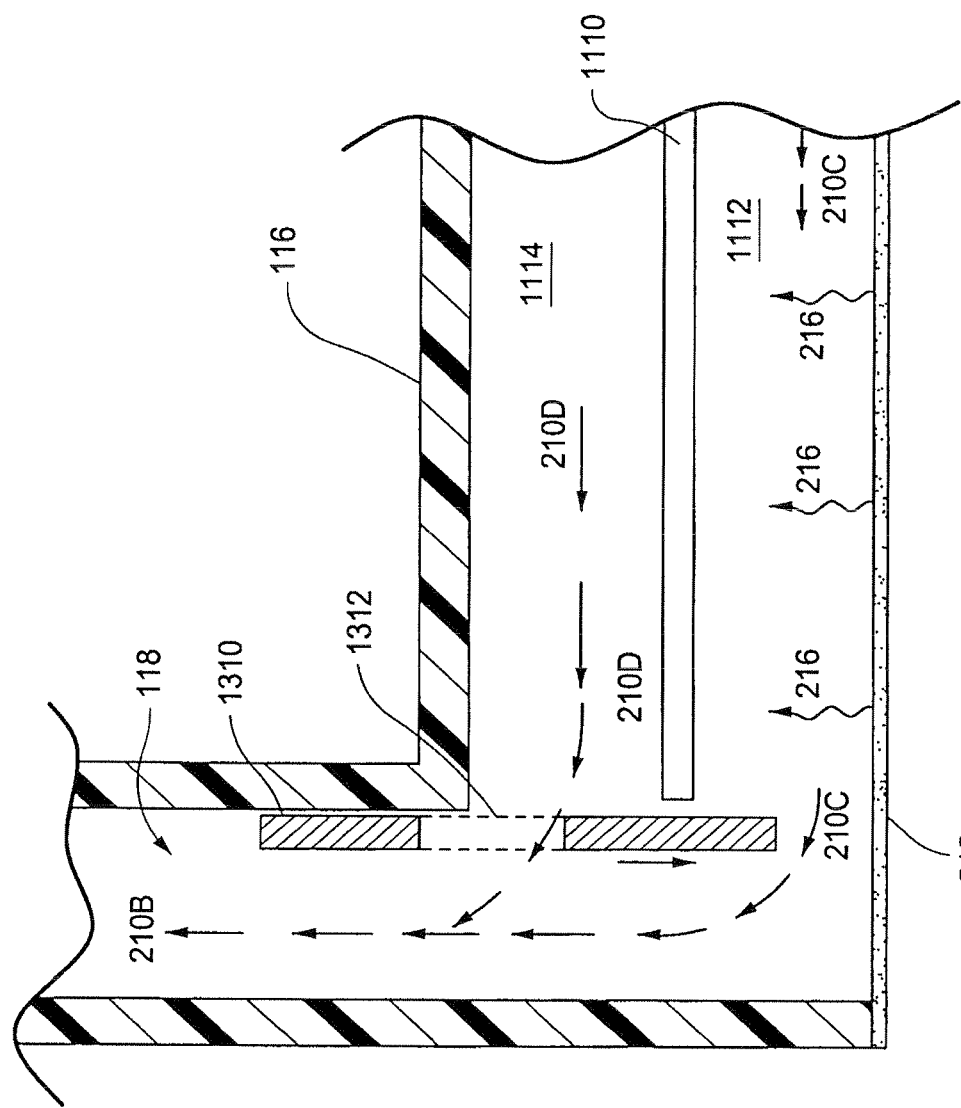
FIG. 14 schematically illustrates the partial shutter position for the humidity control embodiment of FIG. 13.

FIG. 14 shows the shutter 1310 when it has been slid partially downwards in the direction of the arrow. In this position, the aperture 1312 partially obstructs the upper passage layer 1114 such that there is a partial dry gas flow stream 210D. Correspondingly, the lower end of the shutter partially obstructs the lower passage layer 1112 so that there is also a partial humidified gas flow stream 210C. In such a manner, the movement of the sliding shutter can be used to vary the humidity of the humidified gas flow 210B.

Figure 15:
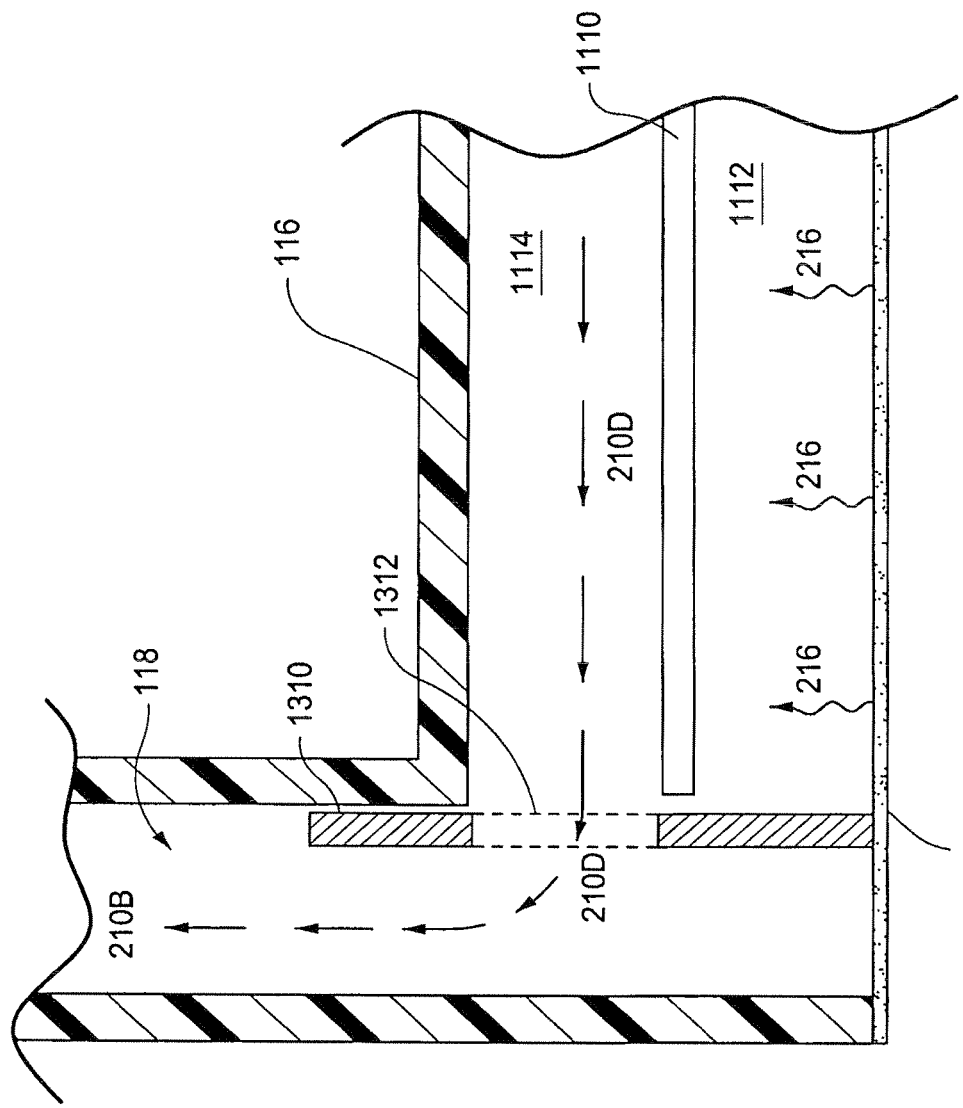
FIG. 15 schematically illustrates the no humidification shutter position for the humidity control embodiment of FIG. 13.

FIG. 15 illustrates the end portion of the sliding shutter 1310 fully obstructing the lower passage layer 1112 whilst the aperture 1312 allows the dry gas stream 210D to flow freely through the upper passage layer 1114. In this shutter 1310 position, there is no additional humidification of the gas flow 210A.

The actuation of the sliding shutter 1310 may be by any suitable electrical and/or mechanical systems (not shown) that are readily available to a person skilled in the art of miniature motion systems. The controlling (not shown) of the sliding shutter 1310 position may be in the same manner as described for the butterfly valve embodiment above.

Figure 16:
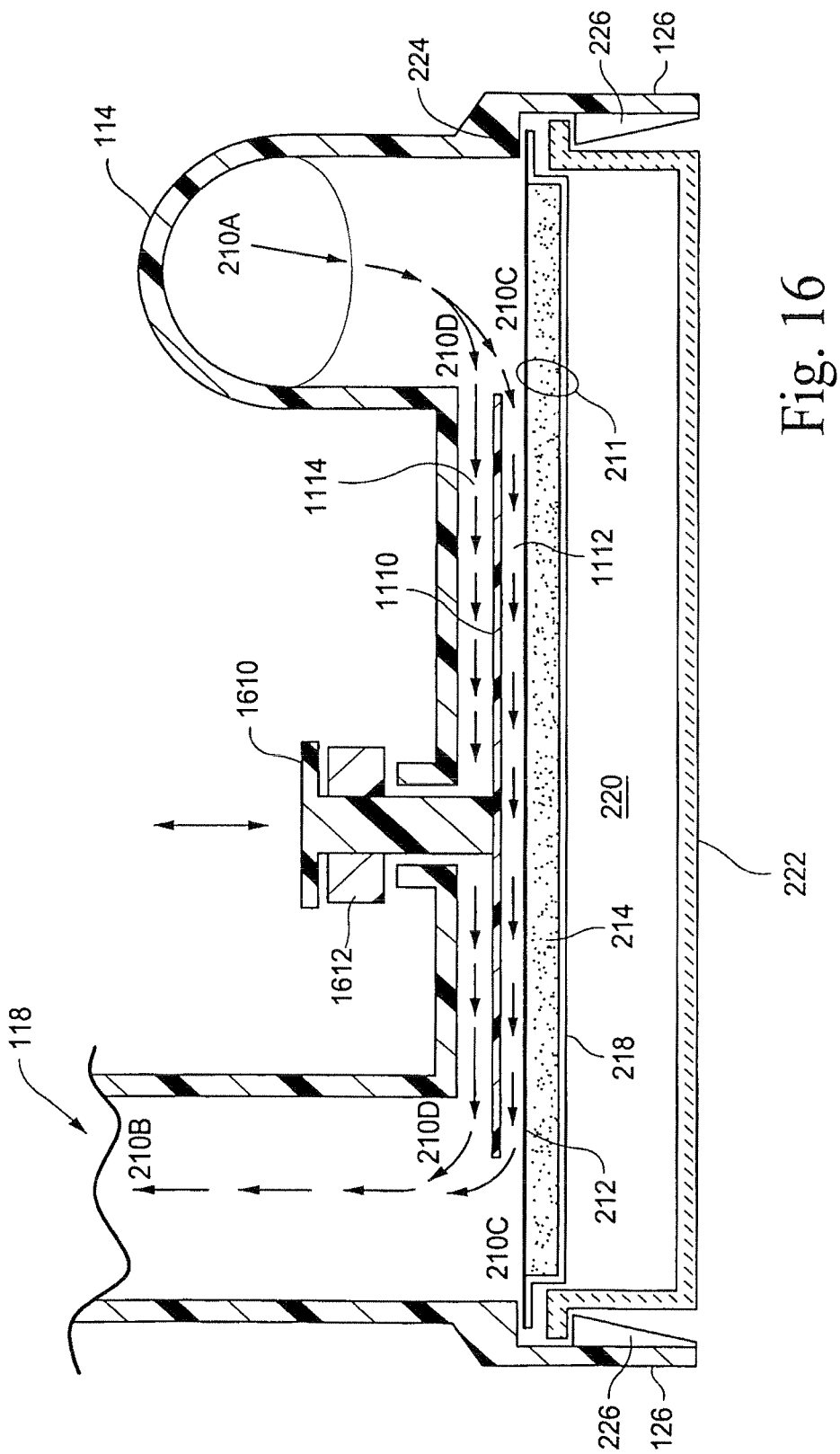
FIG. 16 is a cross-sectional view of a humidifier apparatus including another alternate embodiment for humidity control.

FIG. 16 shows an alternate embodiment to the use of the butterfly valves or sliding shutter for humidity control. In FIG. 16, the plate 1110 is attached to a shaft 1610. The central section of the plate 1110, where the shaft 1610 is attached, is flexible such that if the shaft is moved downwards as indicated by the arrow the lower surface of the plate 1110 may obstruct the lower passage layer 1112 thereby preventing the humidified gas flow stream 210C whilst allowing the dry gas stream 210D to flow. A threaded thumb wheel 1612 may be wound manually to move the shaft 1610 appropriately.

If the shaft 1610 is moved upwards, using the thumb wheel 1612, as indicated by the arrow the upper passage layer 1114 may be obstructed thereby preventing the dry gas stream flow 210D whilst allowing the humidified gas flow stream 210C. The vertical position of the shaft 1610 may thus be used to control the level of humidity of the humidified gas flow 210B.

The actuation of the shaft 1610 may be by any suitable electrical and/or mechanical systems that are readily available to a person skilled in the art of miniature motion systems. The controlling (not shown) of the shaft 1610 vertical position may be in the same manner as described for the butterfly valve and sliding valve embodiments above.

Overlapping Blade Arrangement

Figure 17:
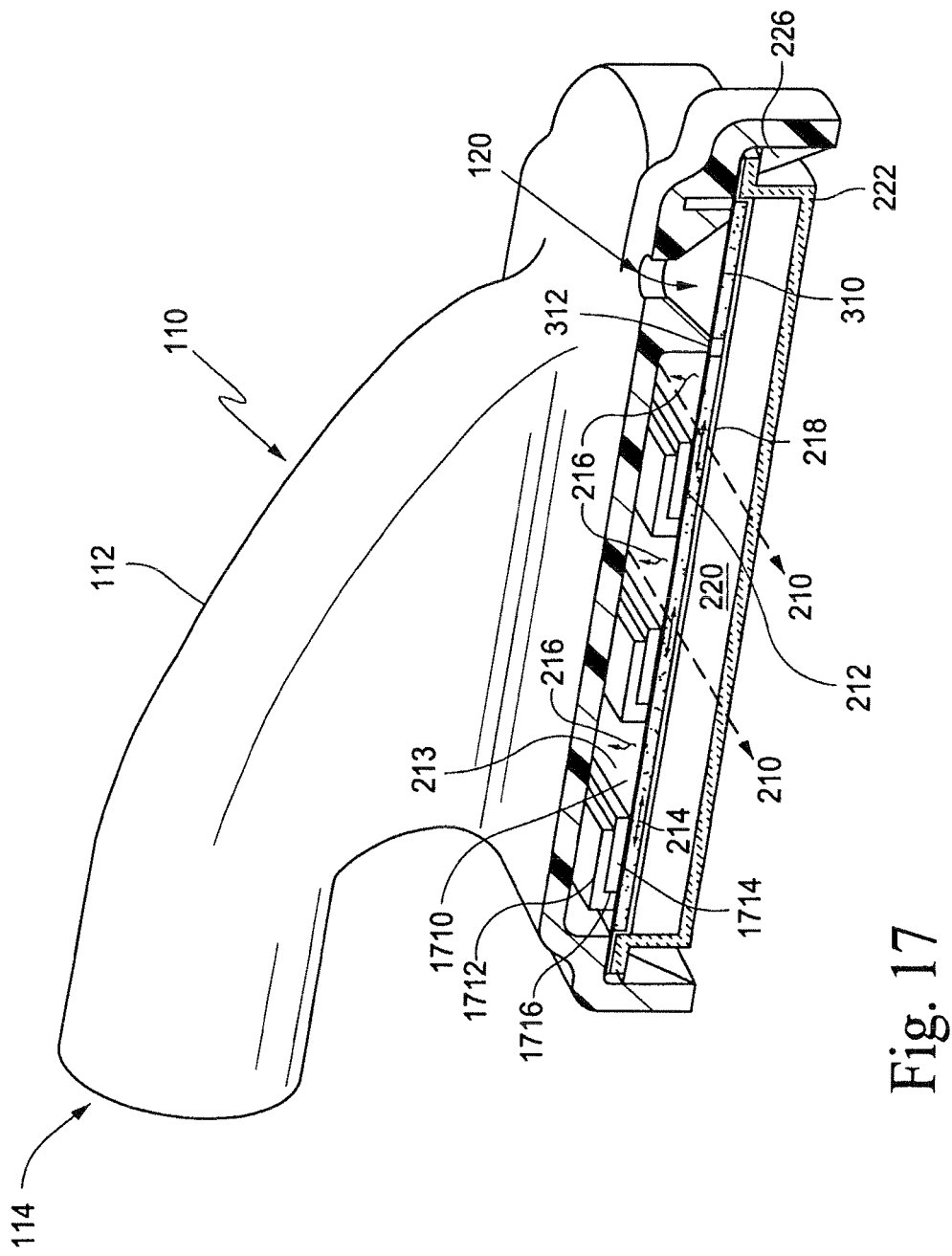
FIG. 17 is a cross-sectional view of a humidifier apparatus including yet another alternate embodiment for humidity control.

FIG. 17 schematically shows yet another alternative embodiment for humidity control. The overlapping blade arrangement comprises of a variable aperture 1710 formed by two overlapping blades, a stationary blade 1712 and a moving blade 1714. The variable aperture controls the amount of interaction between the source of water vapour 216, the first compartment wall 212, and the gas flow path 210 in the gas passage layer 213. FIG. 17 illustrates the fully open aperture state where the moving blade 1714 is fully retracted into the underside recess 1716 of the stationary blade 1712. In the fully open aperture state, all of the water vapour 216 which may issue from the first compartment wall 212 is available for mixing into the gas flow 210 in the gas passage layer 213.

In the fully closed aperture state, the moving blade 1714 would extend from the underside recess 1716 until moving blade 1714 completely covers the variable aperture 1710. In such a fully closed aperture state, there is no transfer of water vapour 216 into the gas flow 210 in the gas passage layer 213, thus no humidification of the gas flow 210 occurs in the humidifier apparatus 110. In between the fully closed and fully open aperture states any number of humidification rates may be obtained by adjusting the position of the moving blade 1714. In the embodiment of FIG. 17, three sets of blades 1712, 1714 with corresponding variable apertures 1710 are shown. Each set of blades may be operated independently or in a synchronised fashion with the other blade sets. The operation of the blades may be by a mechanical device controlled manually or an electro-mechanical device with a computer or analogue circuit servo controller that operates in response to a humidity and/or temperature sensor or any suitable miniature actuation system available to a person skilled in the art.

In further alternative embodiments to the above overlapping blade arrangement, a variable level of exposure of the first compartment wall 212 to the gas flow 210 in the gas passage layer 213 may be achieved by:

A retractable full width blade across the first compartment wall 212.

Two sets of co-axial and overlapping radial blades adjacent to the first compartment wall 212. The radial blade arrangement operates by rotating one or both blade sets in opposite directions so as to open or reduce the radial apertures formed between the radial blades.

A variable aperture may be formed by use of an iris diaphragm.

Heater Apparatus and Humidity Control

In a further alternate embodiment for the humidity control, the heater apparatus 220 embodiments as described above may be used with or without the use of the other humidity control embodiments described above.

Water Reservoir

The water supply may comprise a temporary connection of a single filling, as described with reference to FIG. 3 above, at the start of an overnight therapy session of CPAP for OSA.

Figure 18:
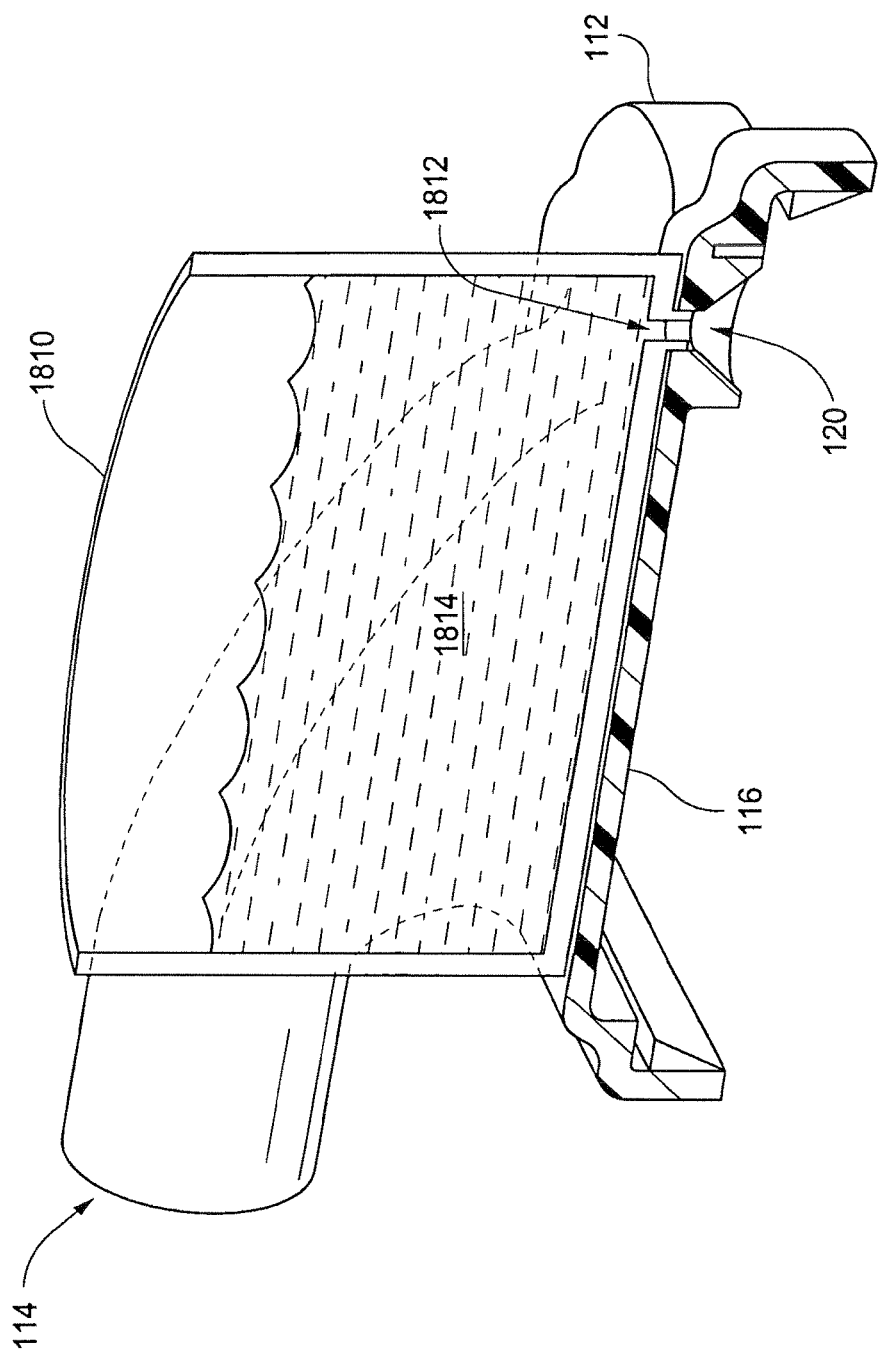
FIG. 18 is a partial, cross-sectional view of a further embodiment of FIG. 3 where an external water reservoir is introduced.

FIG. 18 is a partial, cross-sectional view of a further embodiment of FIG. 3 where an external water reservoir 1810 rests upon the low profile centre section 116 of the housing 112. The external water reservoir 1810 has a drain 1812 which mates with the water inlet passage 120 so that water 1814 may be supplied as a gravity feed to the humidifier apparatus 110. The external water reservoir 1810 may have a capacity of 200 to 1000 ml or may be any desired volume depending on the application and the desired humidification capacity of the humidification apparatus.

In an alternative embodiment, the external water reservoir 1810 may be located elsewhere, such as with other components of the respiratory apparatus. A micro-pump may then be used to supply the water to the water inlet passage 120.

Figure 19:
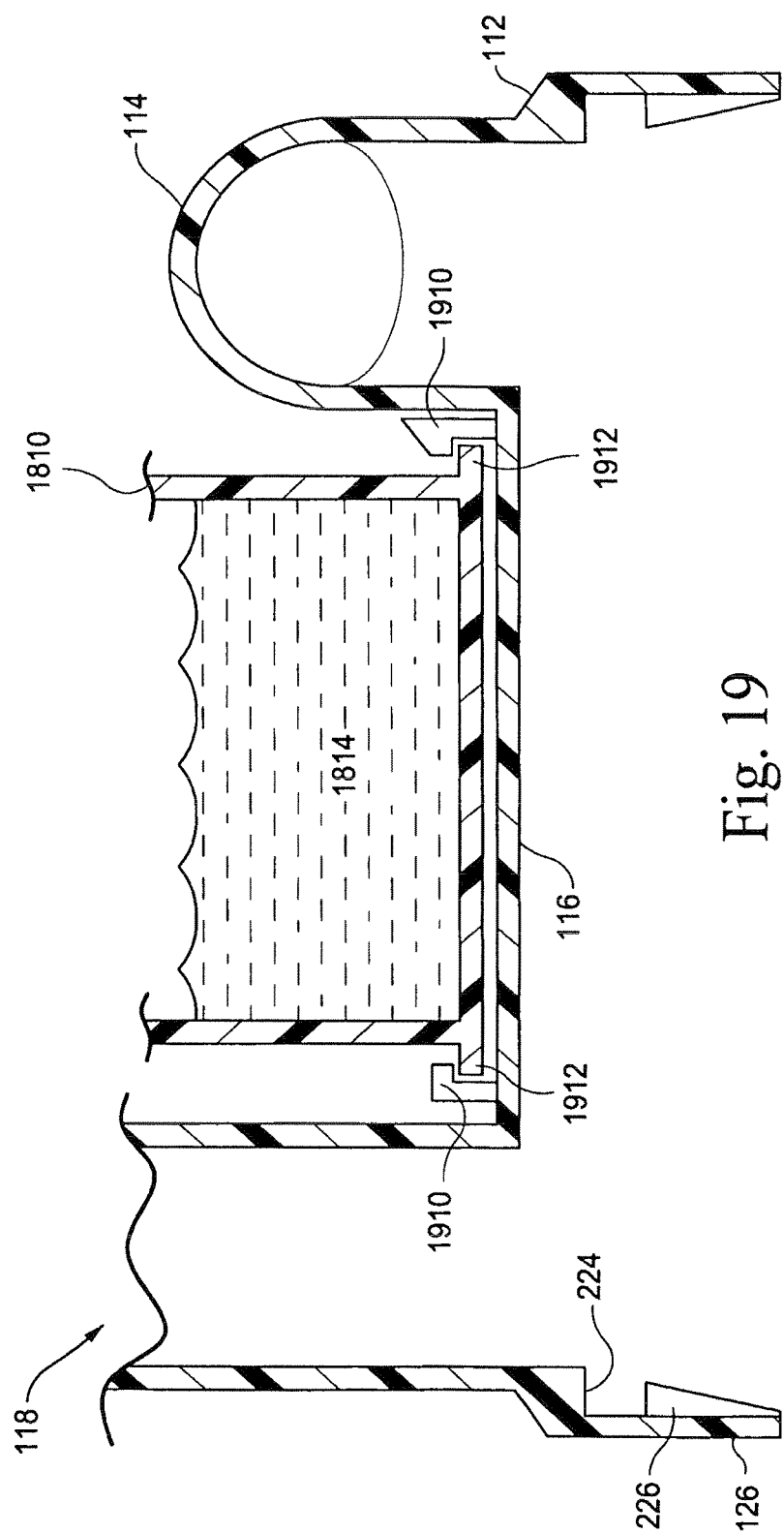
FIG. 19 is a different, partial cross-sectional view of the embodiment of FIG. 18.

FIG. 19 is a different, partial cross-sectional view of the embodiment of FIG. 18. The cross-section taken is as per that for FIG. 2 above. FIG. 19 schematically illustrates a fastening device to secure the water reservoir 1810 to the housing 112. Two or more flexible latches 1910 are used to engage a rim 1912 of the external water reservoir 1810, e.g., snap-fit attachment. The flexibility of the latches 1910 is such that they may be manually pried apart to disengage from the rim 1912 of the water reservoir 1810. Refitting the external water reservoir 1810 may be done by using the snap-clip feature of the latches 1910 as the external water reservoir 1810 is pushed onto the housing 112 at the low profile centre section 116. In an embodiment, the flexible latch may be provided about the entire perimeter.

Application to Existing Respiratory Apparatus

In a further embodiment, the humidifier apparatus may have adaptations which enable it to be accommodated into existing, conventional respiratory apparatus in order to improve the performance of the respiratory apparatus. The overall shape of the humidifier apparatus 110 may be varied in order for it to attach with an existing respiratory apparatus. The base plate 222 may be configured appropriately to make the required thermal and/or electrical contact with the respiratory apparatus. The gas inlet and outlet 114, 118 may be configured to make an appropriate gas seal with the corresponding gas fixtures of the existing respiratory apparatus.

Additional Advantages

The humidifier apparatus 220 with the thin gas passage layer 213 upon a planar water distribution member 211 offers the advantage of having a very high surface area of interaction between the gas flow 210 and the source of water vapour 216. The comparatively small volume of liquid water 214 within the water distribution member 211 compared with conventional tub humidifiers gives an additional advantage of a humidifier apparatus 110 with a very low thermal inertia. Such a system may have a rapid thermal response for the production and cessation of water vapour 216 for the humidification of the gas flow 210.

The use of an envelope about the water layer 214 by the water distribution member 211 reduces the problem of tilting and consequential spillage of water that a conventional tub humidifier is prone to.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A water distribution member for a humidifier apparatus, the water distribution member comprising:
   an envelope formed by a first, substantially planar compartment wall and a second, substantially planar compartment wall joined together along a peripheral edge of the envelope
   a water inlet opening into the envelope formed in a laterally-offset portion of said first substantially planar compartment wall, said laterally-offset portion extending outwardly of remaining portions of said peripheral edge; and
   a heater element configured to be disposed below liquid water when in use, wherein the first substantially planar wall comprises at least in part a semi-permeable membrane, the semi-permeable membrane being configured to prevent liquid water from passing through while being structured to allow water vapour to pass through, and wherein the heater element is integrated with the second substantially planar compartment wall and wherein the second substantially planar wall is configured to conduct heat.

2. The water distribution member according to claim 1, wherein the semi-permeable membrane comprises a finely perforated material.

3. The water distribution member according to claim 1, wherein the semi-permeable membrane comprises a hydrophobic material.

4. The water distribution member according to claim 1, wherein the water distribution member is adapted to be a removable and replaceable fitting to the humidifier apparatus.

5. The water distribution member according to claim 1, further including a water filter in communication with the water inlet.

6. The water distribution member according to claim 1, wherein the heater element comprises a heater plate.

7. The water distribution member according to claim 1, wherein the envelope defines a thin water layer having a thickness of less than about 1 mm.

8. The water distribution member according to claim 1, wherein the envelope defines a thin water layer having a thickness of less than about 5 mm.

9. The water distribution member according to claim 1, wherein the envelope has a volume of less than about 150 ml.

10. The water distribution member according to claim 1, wherein the envelope has a volume of less than about 100 ml.

11. The water distribution member according to claim 1, wherein said second substantially planar compartment wall is comprised of a metal, metal plastic composite or metalized plastic film.

12. The water distribution member according to claim 1 wherein said first and second substantially planar compartment walls are joined by a bonding strip extending about peripheral edges thereof.

13. The water distribution member of claim 1 wherein a filter is located within said water inlet.

14. The water distribution member of claim 13 wherein said filter is supported by one or more ribs.

15. The water distribution member of claim 13 wherein said filter is comprised of a filter disc supported on an underlying support, and wherein the filter disc coincides with said water inlet in said first substantially planar compartment wall.

16. The water distribution member of claim 15 wherein said underlying support is provided with one or more ribs.

17. A water distribution member for a humidifier apparatus comprising an envelope formed by a first, substantially planar compartment wall and a second, substantially planar compartment wall joined together along a peripheral edge of the envelope, and a water inlet opening into the envelope formed in a laterally-offset portion of said first substantially planar compartment wall, said laterally-offset portion extending outwardly of remaining portions of said peripheral edge; wherein the first substantially planar wall comprises at least in part a semi-permeable membrane, the semi-permeable membrane being configured to prevent liquid water while being structured to allow water vapour to pass through, and wherein a heater element is incorporated in the second substantially planar compartment wall.

18. The water distribution member according to claim 17, wherein the heater element comprises an induction receiving element.

19. Humidifier apparatus for a respiratory apparatus, comprising:
a housing;
one or more water supply distribution members removably fitted to the housing, wherein said one or more water supply distribution members comprises an envelope formed by a first upper, substantially planar compartment wall and a second lower, substantially planar compartment wall joined together along a peripheral edge of the envelope, a water inlet opening into the envelope formed in a laterally and outwardly-offset portion of said first substantially planar compartment wall, said laterally and outwardly-offset portion extending outwardly of remaining portions of said peripheral edge, wherein the first substantially planar compartment wall comprises a semi-permeable membrane being configured and arranged to prevent liquid from passing through and being configured to deliver water vapour to one or more gas flow paths defined by the one or more water supply distribution members and the housing; and
a heater apparatus in thermal communication with at least one of the water distribution members, the heater apparatus configured to be disposed below liquid water when in use, wherein the heater apparatus is integrated with the second substantially planar compartment wall.

20. The humidifier apparatus of claim 19 wherein the semi-permeable membrane comprises a hydrophobic material.

21. The humidifier apparatus of claim 19 wherein the heater apparatus comprises a filament or tape heater.

22. The humidifier apparatus of claim 19 wherein the heater apparatus comprises an induction heater.

23. A humidifier apparatus, comprising:
a base plate removably and replaceably attachable to a humidifier housing, the housing having a gas inlet, a gas outlet and a first water inlet;
a heater apparatus provided to the base plate; and
a water distribution member provided to the base plate, the water distribution member including first and second compartment walls joined together along a peripheral edge that define an envelope adapted to receive a supply of water via a second water inlet substantially aligned with said first water inlet, the first water inlet formed in a laterally-offset portion of the first compartment wall, said laterally-offset portion extending outwardly of remaining portions of said peripheral edge, the first compartment wall including a semi-permeable membrane adapted to prevent liquid from passing through and allow water vapour to pass therethrough and the second compartment wall including a thermally conductive wall in thermal communication with the heater apparatus, the heater apparatus configured to be disposed below liquid water when in use, the heater apparatus being integrated with the second compartment wall, and wherein said first water inlet in said housing increases in transverse cross section in an inward direction in order to distribute the water over a filter within the water distribution member.

24. The humidifier apparatus of claim 23 wherein the housing provides a gas flow path, and wherein a plate is located in said gas flow path, above said water distribution member, and configured and arranged to divide the gas flow path into two gas streams such that only one gas stream receives water vapour from the water distribution member and one or more devices are arranged to control the amount of gas flow into one or both gas streams.

25. The humidifier apparatus of claim 24 and further including one or more variable apertures placed between the water supply distribution member and the gas flow path.

26. The humidifier apparatus of claim 25 wherein the one or more variable apertures are structured to regulate the amount of water vapour transferred to the gas flow path.

27. The humidifier apparatus of claim 23, wherein the semi-permeable membrane is hydrophobic.

28. A water distribution member for a humidifier apparatus, the water distribution member comprising:
an envelope formed by a first, substantially planar compartment wall and a second, substantially planar compartment wall joined together along a peripheral edge of the envelope;
a water inlet opening into the envelope formed in a laterally-offset portion of said first substantially planar compartment wall, said laterally-offset portion extending outwardly of remaining portions of said peripheral edge;
wherein the second substantially planar compartment wall includes a thermally conductive wall;
wherein said second substantially planar compartment wall is comprised of a metal, metal plastic composite or metalized plastic film and configured to prevent both liquid water and water vapour from passing therethrough; and
wherein the first substantially planar wall comprises at least in part a semi-permeable membrane, the semi-permeable membrane being configured to prevent liquid water from passing through while being structured to allow water vapour to pass through.

29. The water distribution member of claim 28, wherein the semi-permeable membrane is hydrophobic.

* * * * *